United States Patent
Li et al.

(10) Patent No.: US 12,421,270 B2
(45) Date of Patent: Sep. 23, 2025

(54) OLIGOSACCHARIDE, PREPARATION METHOD THEREFOR, COMPOSITION THEREOF AND USE THEREOF

(71) Applicant: YANTAI DONGCHENG BIOCHEMICALS CO., LTD, Shandong (CN)

(72) Inventors: Zhongjun Li, Beijing (CN); Xiaoming Wu, Shandong (CN); Xiao Zhang, Beijing (CN); Huiying Liu, Beijing (CN); Wang Yao, Beijing (CN); Qingbao Yang, Shandong (CN); Jianqiang Wang, Shandong (CN); Tian He, Shandong (CN)

(73) Assignee: YANTAI DONGCHENG BIOCHEMICALS CO., LTD, Shandong (CN)

( * ) Notice: Subject to any disclaimer, the term of this patent is extended or adjusted under 35 U.S.C. 154(b) by 1051 days.

(21) Appl. No.: 17/775,893

(22) PCT Filed: Jul. 15, 2019

(86) PCT No.: PCT/CN2019/096033
§ 371 (c)(1),
(2) Date: May 11, 2022

(87) PCT Pub. No.: WO2020/015612
PCT Pub. Date: Jan. 23, 2020

(65) Prior Publication Data
US 2023/0029252 A1    Jan. 26, 2023

(30) Foreign Application Priority Data
Jul. 16, 2018    (CN) .......................... 201810778733.6

(51) Int. Cl.
*C07H 11/00*    (2006.01)
*C07H 5/06*    (2006.01)

(52) U.S. Cl.
CPC ............... *C07H 11/00* (2013.01); *C07H 5/06* (2013.01)

(58) Field of Classification Search
CPC ......... C08B 37/0069; C08L 5/08; C12P 19/04
See application file for complete search history.

(56) References Cited

FOREIGN PATENT DOCUMENTS

| CN | 101735336 A | 6/2010 |
| CN | 104557892 A | 4/2015 |
| CN | 106349407 A | 1/2017 |
| CN | 106467563 A | 3/2017 |
| CN | 106645483 A | 5/2017 |
| CN | 107261147 A | 10/2017 |
| CN | 108794653 A | 11/2018 |
| CN | 109912668 A | 6/2019 |
| JP | 6147322 B2 | 6/2017 |

OTHER PUBLICATIONS

Liu et al., Carbohydrate Research, 467, 2018, 45-51, Available online Jul. 27, 2018. (Year: 2018).*
J. Tamura et al., Synthesis of β-D-GalNAc(4,6-diS)(1-4)[α-L-Fuc(2,4-diS)(1-3)]-β-D-GlcA, a novel trisaccharide unit of chondroitin . . . , Tetrahedron Letters 54 (2013) 3940-3943.
Office Action dated Mar. 9, 2021 for Chinese Patent Application No. 201910637636.X and English Translation.
Xiao Zhang et al., Synthesis of Fucosylated Chondroitin Sulfate Nonasaccharide as a Novel Anticoagulant Targeting Intrinsic . . . , Angew. Chem. Int. Ed. 2018, 57, 12880-12885.
Xiao Zhang et al.,Synthesis of fucosylated chondroitin sulfate glycoclusters:a robust route to novel anticoagulant agents, Chem. Eur. J. 10.1002/chem.201705177.
Ricardo P. Vieira et al., Occurrence of a Unique Fucose-branched Chondroitin Sulfate in the Body Wall of a Sea Cucumber*, J. Biol. Chem., 263, 34, Dec. 5, 18176-18183, 1988.
Vitor H.Pomin, Holothurian Fucosylated Chondroitin Sulfate, Mar. Drugs 2014, 12, 232-254.
Longyan Zhao et al., Discovery of an intrinsic tenase complex inhibitor Pure nonasaccharide from fucosylated glycosaminoglycan, PNAS, 2015.
Roberto J. C. Fonseca et al., Fucosylated chondroitin sulfate as a new oral antithrombotic agent, Thromb Haemost 2006; 96: 822-829.
Mingyi Wu et al., Physicochemical characteristics and anticoagulant activities of low molecular weight fractions by free-radical . . . , Food Chemstry. 122 (2010) 716-723.
Charalampos G. Panagos et al., Fucosylated Chondroitin Sulfates from the Body Wall of the Sea Cucumber *Holothuria forskali*, J. Biol. Chem., 289, 41, 28284-28298, Oct. 10, 2014.
Na Gao et al., β-Eliminative depolymerization of the fucosylated chondroitin sulfate and anticoagulant activities of resulting fragment, Carbohydrate Polymers 127(2015)427-437.

(Continued)

*Primary Examiner* — Jonathan S Lau
(74) *Attorney, Agent, or Firm* — Ling Wu; Stephen Yang; Ling and Yang Intellectual Property

(57) ABSTRACT

A fucosylated chondroitin sulfate oligosaccharide having the structure as shown in J, and further disclosed is a method for preparing the fucosylated chondroitin sulfate oligosaccharide: using a chondroitin sulfate A salt as a raw material, sequentially performing enzymolysis, a group protection operation, and glycosylation to synthesize the oligosaccharide compound; the certainty of the described structure allows said oligosaccharide to be applied to the medical field.

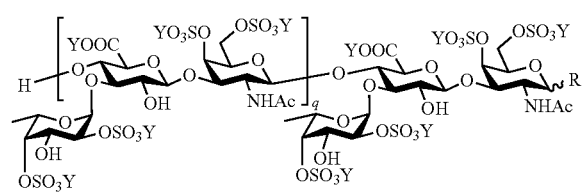

15 Claims, No Drawings

(56) References Cited

OTHER PUBLICATIONS

J. Tamura et al., Synthesis of β-D-GalNAc(4,6-diS)(1-4)[α-L-Fuc(2,4-diS)(1-3)]-β-D-GlcA, a novel trisaccharide unit of chondroitin . . . , Tetrahedron Lett. 54(2013) 3940-3943.

Antonio Laezza et al., Chemical Fucosylation of a Polysaccharide: A Semisynthetic Access to Fucosylated Chondroitin Sulfate, Biomacromolecules, 2015, 16, 2237-2245.

Antonio Laezza et al., A Modular Approach to a Library of Semi-Synthetic Fucosylated Chondroitin Sulfate Polysaccharides with Different . . . , Chem. Eur. J. 2016, 22, 1-13.

S. Chen et al., Comparison of structures and anticoagulant activities of fucosylated chondroitin sulfates from different sea cucumbers, Carbohydrate Polymers, 83(2011) 688-696.

L. Bastide et al., Chemo-bacterial synthesis and immunoreactivity of a brain HNK-1 analogue, Carbohydrate Research 346 (2011) 348-351.

European Serch Report dated Sep. 15, 2021 for European Patent Application No. 19838347.3.

International Search Report for PCT/CN2019/096033 Mailed Oct. 12, 2019.

Office Action dated Feb. 22, 2022 for Japanese Patent Application No. 2021-525352 and English Translation.

Notice of Allowance dated Oct. 20, 2021 for Chinese Patent Application No. 201910637636.X and English Translation.

S. Kohling et al., Chemoenzymatic Synthesis of Nonasulfated Tetrahyaluronan with a Paramagnetic Tag for Studying Its Complex with . . . , Chem. Eur. J. 2016, 22, 5563-5574.

Y. Hua et al., Synthesis and biological activities of octyl 2,3,4-tri-O-sulfo-α-L-fucopyranosyl-(1->3)-2,4-di-O-sulfo-α-L- . . . ,Carbohydrate Research 339 (2004) 867-872.

R. Suresh et al., Synthesis of Isoquinoline Derivatives From β-Hydroxyarylethanamides, Synthetic Communications, 45:1696-1703, 2015.

Zhang et al., "Synthesis and anticoagulant activity of glycosylated thiol chondroitin oligosaccharide clusters", The 11th National Natural Organic Chemistry Conference of the Chinese Chemical Society, Published on Sep. 30, 2016.

* cited by examiner

OLIGOSACCHARIDE, PREPARATION METHOD THEREFOR, COMPOSITION THEREOF AND USE THEREOF

CROSS-REFERENCE TO RELATED APPLICATIONS

The present application is a U.S. National Phase Entry of International PCT Application No. PCT/CN2019/096033 having an international filing date of Jul. 15, 2019, which claims priority to Chinese Patent Application No. 201810778733.6 filed on Jul. 16, 2018. The present application claims priority and the benefit of the above-identified applications and the above-identified applications are incorporated by reference herein in their entirety.

TECHNICAL FIELD

The application relates but is not limited to the technical field of medicinal chemistry, and more specifically, relates to fucosylated chondroitin sulfate oligosaccharides, preparation method and compositions thereof, and use of the compound.

BACKGROUND

Fucosylated chondroitin sulfate is a class of glycosaminoglycan extracted from sea cucumber. Chondroitin sulfate polysaccharide is the backbone of the structure while fucose side chain is attached to the hydroxyl group of the 3-position of the uronic acid, and there are sulfonate groups at different positions, thereby forming trisaccharide repeating units (J. Biol. Chem. 1988, 263, 18176).

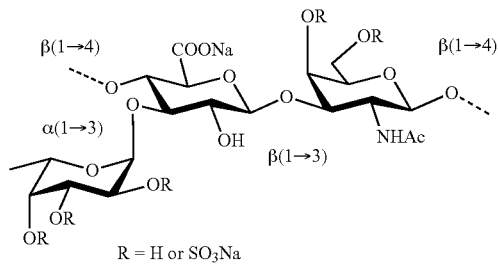

Fucosylated chondroitin sulfate has biological functions such as anticoagulation, anti-HIV, anti-inflammation, wound repair and others (Mar. Drugs 2014, 12, 232). Its anticoagulant activity adopts a different pharmacological mechanism compared with that of heparin drugs, and it significantly reduces the risk of bleeding (P Natl Acad Sci USA, 2015, 112, 8284), and is orally effective (Thromb. Haemostasis, 2006, 96, 822), and thereby it has good development prospects and significant research values.

Fucosylated chondroitin sulfate polysaccharide extracted from nature has side effects of factor XII activation and thrombocytopenia. In order to solve this problem, various methods for degrading the polysaccharide have been developed, including free radical degradation (Food. Chem, 2010, 122, 716), photochemical degradation (J. Biol. Chem, 2014, 289, 28284) and β-elimination degradation (Carbohydr. Polym, 2015, 127, 427), which reduce the side effects of polysaccharide while retaining the anticoagulant activity. However, since the oligosaccharides obtained by extraction or degradation are microscopically heterogeneous and there is risk of contamination, it is difficult to fulfill the requirements for clinical administration in terms of quality control, which significantly limits its transformation into a medicine. Therefore, obtaining fucosylated chondroitin sulfate oligosaccharide with a defined structure and high purity by a synthetic approach is the only effective way for conducting further researches in biology and medicinal chemistry.

In prior arts, fucosylated chondroitin sulfate trisaccharide was synthesized using glucose, N-acetylgalactosamine and fucose as raw materials, and oligosaccharide assembly is achieved through protecting group attachment and glycosylation. Starting from the sugar building blocks, there are in total 16 steps in the reaction, with a total yield of 0.95% (Tetrahedron. Lett, 2013, 54, 3940). There is still much room for optimization. Natural polysaccharide analogs were obtained by non-selective fucosylation of the raw material chondroitin polysaccharide, but their structures are still uncertain (Biomacromolecules, 2015, 16, 2237; Chem. Eur. J, 2016, 22, 18215). Therefore, it is of great significance to develop a new chemical synthesis method for fucosylated chondroitin sulfate oligosaccharide.

In addition, studies have shown that the anticoagulant activity of fucosylated chondroitin sulfate is positively related to its molecular weight (J. Biol, Chem, 2014, 289, 28284), and the pattern of sulfation on the fucose side chain significantly affects its activity. Studies have shown that 2,4-O-sulfated structure of the fucose side chain has the best anticoagulant activity (Carbohydr. Polym, 2011, 83, 688). However, all the current research results are based on oligosaccharides obtained by extraction or degradation method, and the structure is microscopically heterogeneous, so it is impossible to draw an exact conclusion and obtain a clear structure-activity relationship. Therefore, obtaining fucosylated chondroitin sulfate oligosaccharide with a defined structure and high purity by a synthetic approach is of great significance for facilitating medicinal chemistry research of fucosylated chondroitin sulfate.

SUMMARY OF INVENTION

The inventors, using inexpensive chondroitin sulfate polysaccharide as raw material, obtained fucosylated chondroitin sulfate oligosaccharide through enzymolysis, chemical modification and fucosylation. The synthetic route is simple and has a high efficiency, and the structure of the compound is definite, and the synthetic route has overcome the deficiencies in prior arts.

In one aspect, the present application provides a fucosylated chondroitin sulfate oligosaccharide shown as formula J:

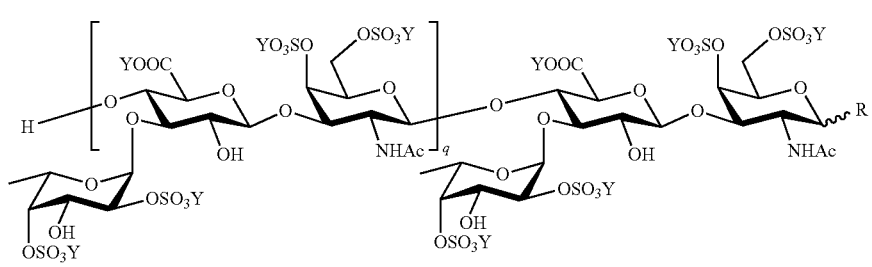

In formula J, Ac is acetyl; q is a positive integer and q≤10; Y is H, alkali metal, alkaline earth metal, or N(R$_6$)$_4$, wherein R$_6$ is C1-C4 alkyl; R is azido, C1-C4 alkoxy, phenoxy, C1-C4 alkylthio, C1-C4 alkanoylthio, benzoyloxy or benzoylthio.

In a second aspect, the present application provides a synthesis method for the fucosylated chondroitin sulfate oligosaccharide described above. The fucosylated chondroitin sulfate oligosaccharide may be obtained by using chondroitin sulfate polysaccharide as raw material, and through enzymolysis, chemical modification and fucosylation.

In a third aspect, the present application provides intermediate compounds for synthesizing fucosylated chondroitin sulfate oligosaccharide.

In a fourth aspect, the present application provides a pharmaceutical composition including the fucosylated chondroitin sulfate oligosaccharide described above.

In a fifth aspect, the present application provides use of the fucosylated chondroitin sulfate oligosaccharide described above.

DETAILED DESCRIPTION

In an embodiment of the present application, the present application provides a fucosylated chondroitin sulfate oligosaccharide shown as formula J:

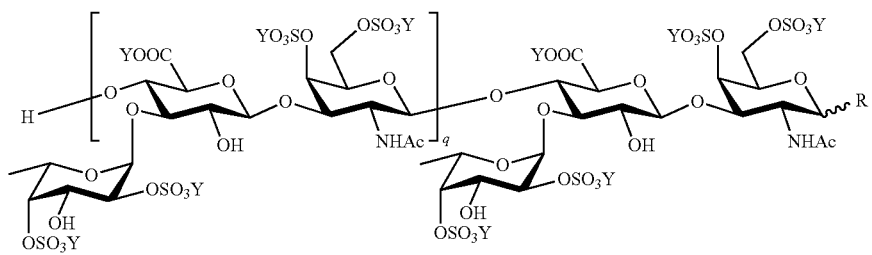

In formula J, Ac is acetyl; q is a positive integer and q≤10; Y is H, alkali metal, alkaline earth metal, or N(R$_6$)$_4$, wherein R$_6$ is C1-C4 alkyl; R is azido, C1-C4 alkoxy, phenoxy, C1-C4 alkylthio, C1-C4 alkanoylthio, benzoyloxy or benzoylthio.

In some embodiments of the present application, the present application provides a fucosylated chondroitin sulfate oligosaccharide shown as formula J, wherein when R is azido, phenoxy, C1-C4 alkylthio, C1-C4 alkanoylthio, benzoyloxy, or benzoylthio, ⌇ is in configuration; and when R is C1-C4 alkoxy, ⌇ is in α configuration.

In some embodiments of the present application, the present application provides a fucosylated chondroitin sulfate oligosaccharide shown as formula J, wherein R is azido and ⌇ is in β configuration.

In some embodiments of the present application, the present application provides a fucosylated chondroitin sulfate oligosaccharide shown as formula J, wherein R is methyl and ⌇ is in α configuration.

In some embodiments of the present application, the present application provides a fucosylated chondroitin sulfate oligosaccharide shown as formula J, wherein in formula J, q is 1, 2, 3 or 4; Y is H, sodium, lithium, potassium, calcium or magnesium; R is azido, and ⌇ is in β configuration; or, R is methyl, and ⌇ is in α configuration.

In some embodiments of the present application, the present application provides a fucosylated chondroitin sulfate oligosaccharide shown as formula J, wherein in formula J, q is 1, 2, 3 or 4; Y is sodium; R is azido, and ⌇ is in β configuration; or, R is methyl, and ⌇ is in α configuration.

In a particularly preferred embodiment of the present application, the fucosylated chondroitin sulfate oligosaccharide shown as formula J provided by the present application is selected from one of the following compounds:

azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]} decasodium salt;

azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]} pentadecasodium salt; and methyl-{(2,4-di-O-sulfo-α-L-fucosyl)-(1→3)-(β-D-glu-copyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-α-D-galactopyranosyl)]} decasodium salt.

In a second aspect, in an embodiment of the present application, the present application provides a synthesis method of the fucosylated chondroitin sulfate oligosaccharide described above, including the following steps:

(1) removing the sulfonate group from a compound of formula A (i.e., M salt of chondroitin sulfate, and preferably, M is sodium) in a C1-C4 alkanol solution of an inorganic acid, and treating with MOH base, to obtain a compound of formula B; wherein m in formula A and n in formula B are positive integers, and 20≤n≤m;

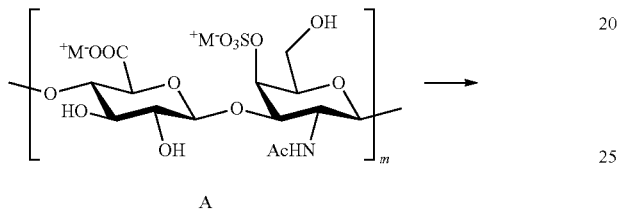

A

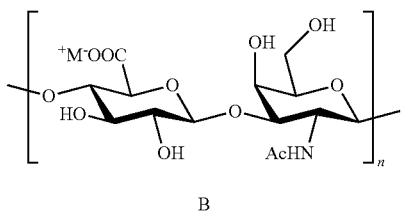

B (2) subjecting the compound of formula B (i.e., M salt of chondroitin sulfate, and preferably, M is sodium) in a weakly acidic buffer solution containing sodium chloride, and by the activity of hyaluronidase, to obtain a compound of formula C; wherein the hyaluronidase is originated from animal testis, selected from bovine testis or sheep testis; preferably from bovine testis, with an activity of 400-1000 IU/mg; q is a positive integer from 1-10;

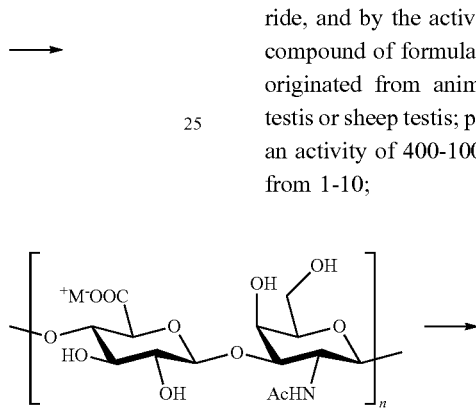

B

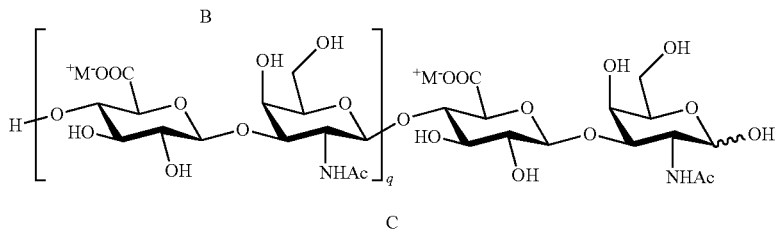

C (3) subjecting the compound of formula C to react with a nucleophilic reagent RX (such as sodium azide, C1-C4 alkoxy sodium, phenoxy sodium, C1-C4 alkylthio sodium, C1-C4 alkanoylthio sodium, sodium benzoate, or benzoylthio sodium) to obtain a compound of formula D;

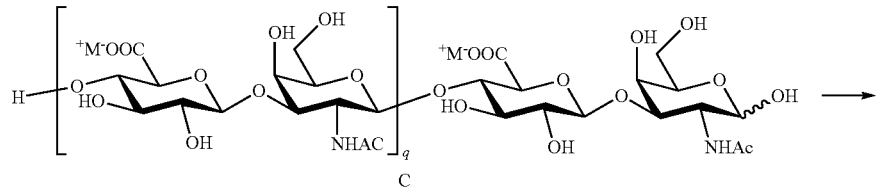

C

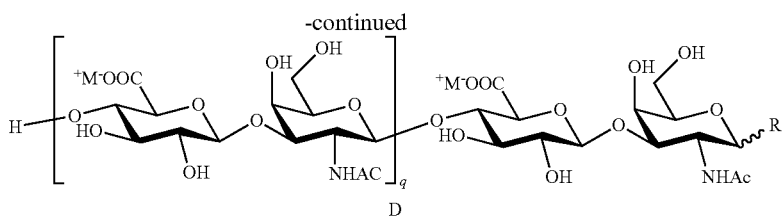

D (4) subjecting the compound of formula D to selective protection of 4, 6 dihydroxy of the acetylgalactosamine residue of the compound of formula D, in the presence of $R_1C(O)H$ or $R_1C(O)H$ dialiphatic alcohol (e.g., $R_1CH(OCH_3)_2$), and under acid catalysis, to obtain a compound of formula E;

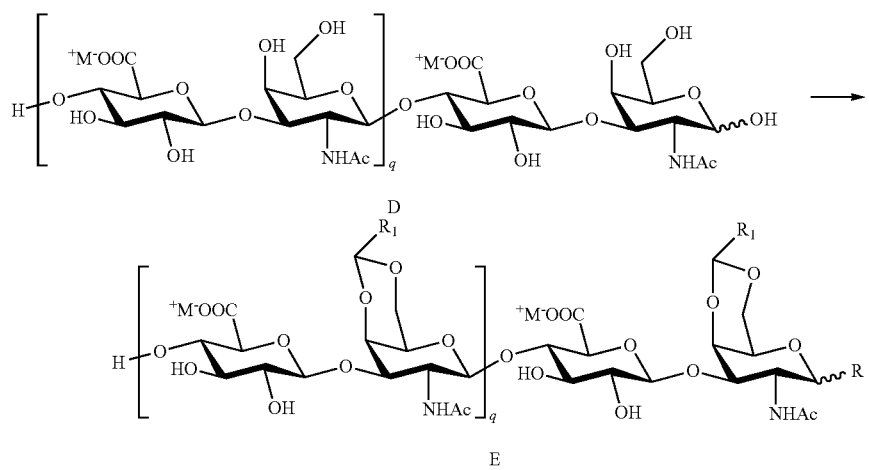

(5) cyclizing the compound of formula E with the presence of anhydride $R_2$—O—$R_2$, followed by lactone ring opening in $R_3OH$ solution under base catalysis, to obtain a compound of formula F;

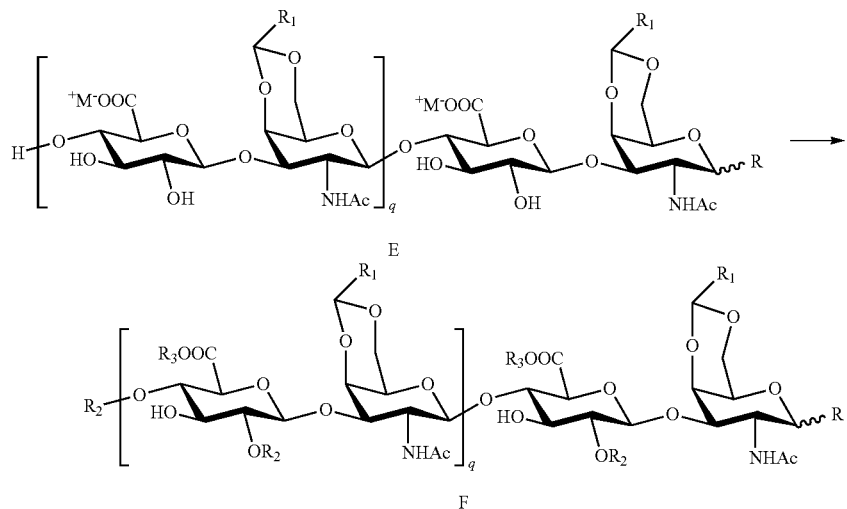

(6) subjecting the compound of formula F to reaction with a compound of formula G as fucose donor, under acid catalysis, to obtain a compound of formula H;

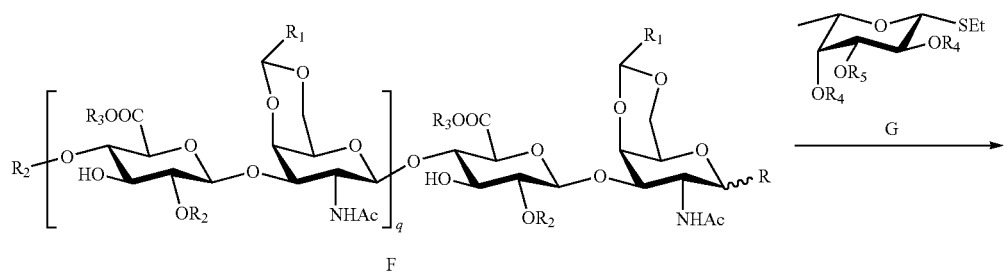
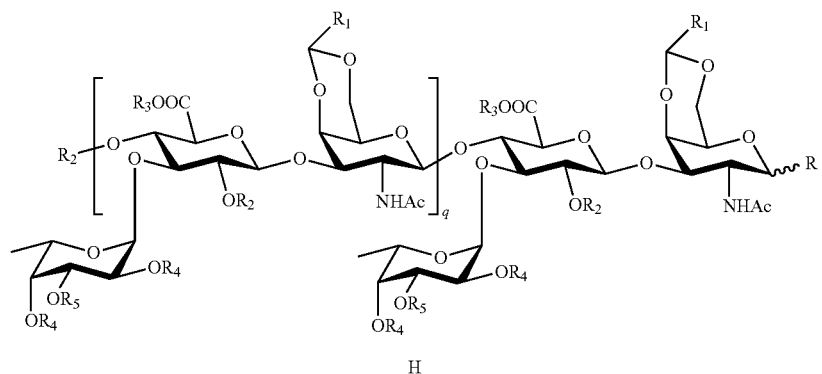
(7) removing galactosamine 4,6-OH protection from the compound of formula H with the presence of an acid, followed by selectively removing the protective group R₄ on the fucose, to obtain a compound of formula I;
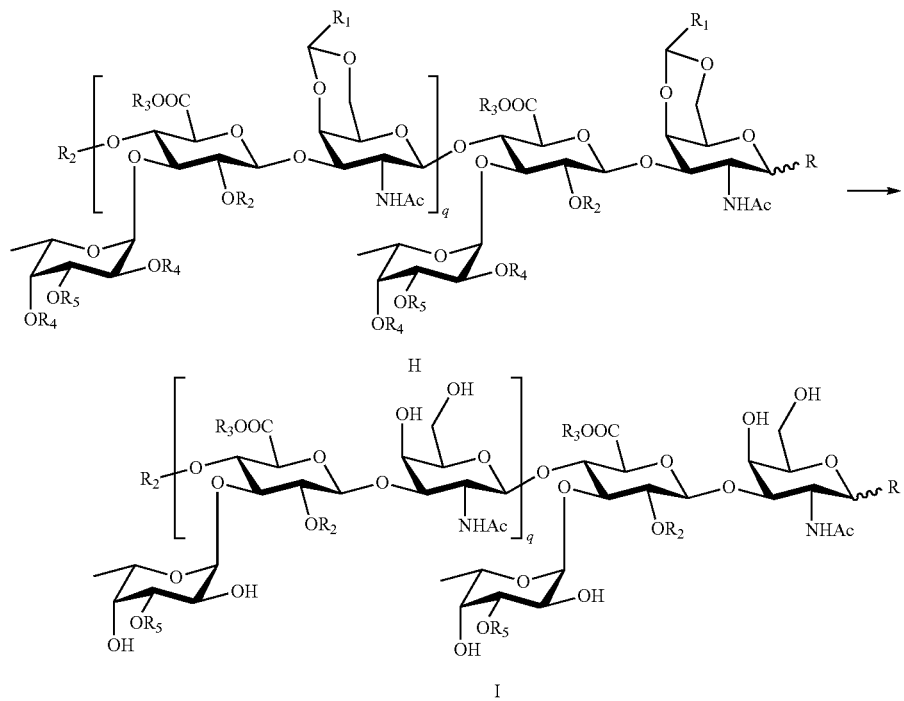
(8) subjecting the compound of formula I to sulfation and deprotection, to obtain the compound of formula J';

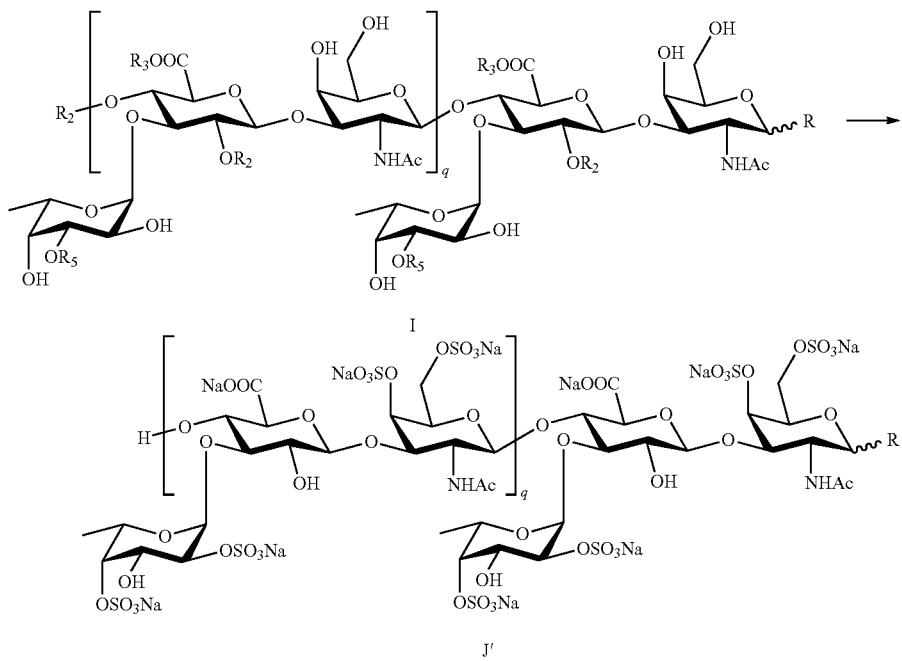

wherein, in the compounds of formula D to formula J and RX, R is azido, C1-C4 alkoxy, phenoxy, C1-C4 alkylthio, C1-C4 alkanoylthio, benzoyloxy or benzoylthio; preferably, when R is azido, phenoxy, C1-C4 alkylthio, C1-C4 alkanoylthio, benzoyloxy, or benzoylthio, ∼∼∼ is in β configuration; when R is C1-C4 alkoxy, ∼∼∼ is in α configuration;

X in RX is hydrogen or alkali metal (sodium, potassium or lithium);

in $R_1C(O)H$ or $R_1C(O)H$ dialiphatic alcohol and the compounds of formula E to formula H, $R_1$ is unsubstituted phenyl or substituted phenyl; wherein, the substituted phenyl refers to a benzene ring being substituted by one or two or more substituents selected from one or more of halogen (e.g., fluorine, chlorine, bromine or iodine), nitro, C1-C4 alkyl (e.g., methyl, ethyl, n-propyl, isopropyl, n-butoxy, isobutoxy or tert-butoxy), C1-C4 haloalkyl (e.g., trifluoromethyl) and C1-C4 alkoxy (e.g., methoxy, ethoxy, n-propoxy, isopropoxy, n-butoxy, iso-butoxy, or tert-butoxy); and, optionally, the substituent is at any position of the benzene ring; preferably, $R_1$ is selected from one of phenyl, 4-methoxyphenyl, 4-chlorophenyl and 4-bromophenyl, more preferably, $R_1$ is selected from one of phenyl and 4-methoxyphenyl; wherein, the aliphatic alcohol in $R_1C(O)H$ or $R_1C(O)H$ dialiphatic alcohol is C1-C4 alkanol (e.g., methyl, ethyl, n-propyl, isopropyl, n-butyl, isobutyl or tert-butyl), preferably methanol;

in the anhydride $R_2$—O—$R_2$, or the compounds of formula F to formula I, $R_2$ is selected from one of aliphatic acyl, unsubstituted benzoyl or substituted benzoyl, and acetylpropionyl; wherein, the aliphatic acyl refers to C2-C6 alkanoyl (e.g., acetyl, propionyl, n-butyryl, isobutyryl, n-valeryl, pivaloyl or n-caproyl); the substituted benzoyl refers to the benzene ring being substituted by one or two or more substituents selected from one or more of halogen (e.g., fluorine, chlorine, bromine or iodine), nitro, C1-C4 alkyl (e.g., methyl, ethyl, n-propyl, isopropyl, n-butyl, isobutyl or tert-butyl), C1-C4 haloalkyl (e.g., trifluoromethyl) and C1-C4 alkoxy (e.g., methoxy, ethoxy, n-propoxy, isopropoxy, n-butoxy, iso-butoxy, or tert-butoxy); and, optionally, the substituent is at any position of the benzene ring; preferably, $R_2$ is selected from one of acetyl, benzoyl, 4-chlorobenzoyl and 4-bromobenzoyl, more preferably $R_2$ is selected from one of acetyl and benzoyl;

in $R_3OH$, or the compounds of formula F to formula I, $R_3$ is selected from one of unsubstituted benzyl or substituted benzyl, C1-C4 alkyl, C1-C4 alkoxy and allyl; wherein substituted benzyl refers to the benzene ring being substituted by one or two or more substituents selected from one or more of halogen (e.g., fluorine, chlorine, bromine or iodine), nitro, C1-C4 alkyl (e.g., methyl, ethyl, n-propyl, isopropyl, n-butyl, isobutyl or tert-butyl), C1-C4 haloalkyl (e.g., trifluoromethyl), and C1-C4 alkoxy (e.g., methoxy, ethoxy, n-propoxy, isopropoxy, n-butoxy, iso-butoxy, or tert-butoxy); and, optionally, the substituent is at any position of the benzene ring; preferably, $R_3$ is selected from one of methyl, ethyl, allyl, benzyl and 4-methoxybenzyl, more preferably $R_3$ is selected from one of methyl, ethyl and benzyl;

in the compounds of formula G to formula H, $R_4$ is selected from unsubstituted benzyl or substituted benzyl; wherein the substituted benzyl refers to the benzene ring being substituted by one or two or more substituents selected from one or more of halogen (e.g., fluorine, chlorine, bromine or iodine), nitro, C1-C4 alkyl (e.g., methyl, ethyl, n-propyl, isopropyl, n-butyl, isobutyl or tert-butyl), C1-C4 haloalkyl (e.g., trifluoromethyl), and C1-C4 alkoxy (e.g., methoxy, ethoxy, n-propoxy, isopropoxy, n-butoxy, iso-butoxy, or tert-butoxy); and, optionally, the substituent is at any position of the benzene ring; preferably, $R_4$ is selected from benzyl and p-methoxybenzyl;

in the compounds of formula G to formula I, $R_5$ is selected from one of aliphatic acyl, unsubstituted benzoyl or substituted benzoyl, and acetylpropionyl; wherein aliphatic acyl refers to C2-C6 alkanoyl (e.g., acetyl, propionyl, n-butyryl, isobutyryl, n-valeryl, pivaloyl or n-caproyl); substituted benzoyl refers to the benzene ring being substituted by one or two or more substituents selected from one or more of halogen (e.g., fluorine, chlorine, bromine or iodine), nitro, C1-C4 alkyl (e.g., methyl, ethyl, n-propyl, isopropyl, n-butyl, isobutyl or tert-butyl), C1-C4 haloalkyl (e.g., trifluoromethyl) and C1-C4 alkoxy (e.g., methoxy, ethoxy, n-propoxy, isopropoxy, n-butoxy, iso-butoxy, or tert-butoxy); and, optionally, the substituent is at any position of the benzene ring; preferably, $R_5$ is selected from one of acetyl, benzoyl, acetylpropionyl, 4-chlorobenzoyl and 4-bromobenzoyl, more preferably $R_5$ is acetyl, acetylpropionyl or benzoyl;

Et in the compound of formula G is ethyl;

In formula A to formula D and MOH base, M is sodium, potassium, lithium or calcium (preferably selected from sodium).

In an embodiment provided by the present application, according to the synthesis method of fucosylated chondroitin sulfate oligosaccharide provided by the present application, after a compound of formula J', i.e. compound J in which Y is Na, is obtained, a compound of formula J in which Y is not Na can also be obtained according to conventional technology in the field.

In the synthesis method of fucosylated chondroitin sulfate oligosaccharide provided by the present application, in step (1), source of the inorganic acid is selected from one or more of hydrogen chloride, sulfuric acid, nitric acid and phosphoric acid, preferably being hydrogen chloride or sulfuric acid; the C1-C4 alkanol is methanol or ethanol, preferably selected from methanol; and the MOH base is NaOH, KOH, or LiOH, preferably NaOH.

In the synthesis method of fucosylated chondroitin sulfate oligosaccharide provided by the present application, in step (2), preferably, the hyaluronidase has an activity of 400-1000 IU/mg, and is added in an amount of 2.0-3.0% of the mass of chondroitin, and the reaction temperature is 37° C.; weakly acidic refers to the pH value of the buffer solution being 3.0-6.5 (preferably selected from 5.0-5.2); the buffer solution refers to one of: acetic acid—sodium acetate buffer, acetic acid—potassium acetate buffer, sodium dihydrogen phosphate—disodium hydrogen phosphate buffer or potassium dihydrogen phosphate—dipotassium hydrogen phosphate buffer, preferably selected from acetic acid—sodium acetate buffer; the concentration of the buffer is selected from 0.01 M to 1 M, and preferably is selected from 0.1 M acetic acid—sodium acetate buffer; sodium chloride of a certain concentration refers to a concentration of sodium chloride selected from 0.05 M to 0.5 M, preferably selected from 0.15 M; the hyaluronidase is selected from hyaluronidase originating from animal testis, for example, hyaluronidase originating from bovine testis purchased from Sigma-Aldrich.

In the synthesis method of fucosylated chondroitin sulfate oligosaccharide provided by the present application, in step (3), when RX is sodium azide, sodium phenolate, sodium C1-C4 alkylthio, sodium C1-C4 alkanoylthio, sodium benzoate or sodium benzoylthio, the compound of formula C reacts with sodium azide, sodium phenolate, sodium C1-C4 alkylthio, sodium C1-C4 alkanoylthio, sodium benzoate or sodium benzoylthio, in a basic solution with the presence of 2-chloro-1,3-dimethyl imidazoline chloride, to obtain a compound of formula D, and in the compound of formula D, ⁓ is in β configuration; wherein the organic base used in the basic solution is selected from one or more of triethylamine, N-methylmorpholine, pyridine, 2,6-dimethylpyridine and diisopropylethylamine; when RX is C1-C4 alkyl alcohol, the compound of formula C undergoes reaction overnight in an alkyl alcohol solution of HCl, and then releases carboxyl under a basic condition, to obtain the compound of formula D, and in the compound of formula D, ⁓ is in α configuration; wherein the inorganic base used under the basic condition is selected from one or more of sodium hydroxide, potassium hydroxide and lithium hydroxide.

In the synthesis method of fucosylated chondroitin sulfate oligosaccharide provided by the present application, in step (4), under acid catalysis refers to being in the presence of the following protic acids or Lewis acids: preferably, in the presence of p-toluenesulfonic acid or camphorsulfonic acid.

In the synthesis method of fucosylated chondroitin sulfate oligosaccharide provided by the present application, the base used in step (5) is selected from one or more of sodium methoxide and sodium acetate.

In the synthesis method of fucosylated chondroitin sulfate oligosaccharide provided by the present application, in step (6), under acid catalysis refers to being in the presence of the following protic acids or Lewis acids: one or more selected from trifluoromethanesulfonic acid, alkylsilyl trifluoromethanesulfonate, metal salt of trifluoromethanesulfonate and boron trifluoride etherate, preferably selected from metal salt of trifluoromethanesulfonate; the reaction in step (6) is carried out in an organic solvent selected from one or more of dichloromethane, N, N-dimethylformamide, chloroform, diethyl ether and toluene, preferably from a mixed solvent of dichloromethane and N, N-dimethylformamide, wherein the volume ratio of dichloromethane to N, N-dimethylformamide is 3:1-2:1;

In the synthesis method of fucosylated chondroitin sulfate oligosaccharide provided by the present application, the acid used in the step (7) is selected from one or more of acetic acid, camphorsulfonic acid and p-toluenesulfonic acid. The reagent used for "selectively removing the protective group $R_4$ on fucose" is selected from one of ceric ammonium nitrate and 2,3-dichloro-5,6-dicyano-p-benzoquinone (DDQ).

In the synthesis method for the fucosylated chondroitin sulfate oligosaccharide provided by the application, in step (8), the reagent used for sulfation is selected from one of pyridine sulfur trioxide complex, sulfur trioxide trimethylamine complex and sulfur trioxide triethylamine complex, and the sulfation is optionally carried out in anhydrous pyridine or anhydrous DMF; deprotection is carry out in a mixed solvent of tetrahydrofuran and water. Volumn ratio of tetrahydrofuran to water is 3:1-2:1, and the base is one or two of lithium hydroxide and sodium hydroxide.

In a third aspect, the present application provides an intermediate compound for synthesizing fucosylated chondroitin sulfate oligosaccharide. The intermediate compound is selected from one of the compounds of formula D to formula I:

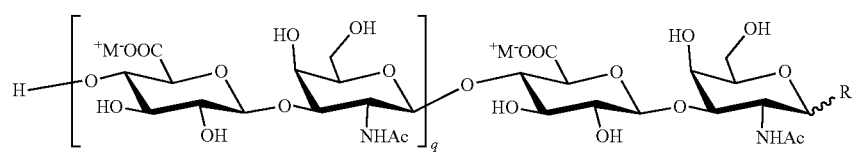

D

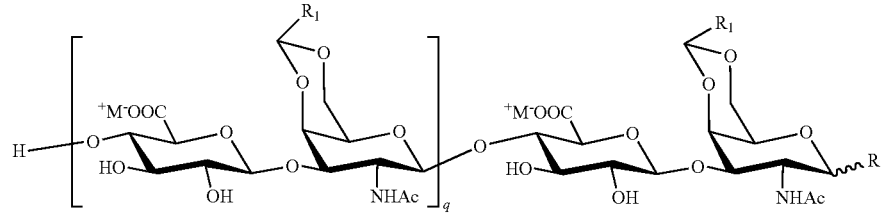

E

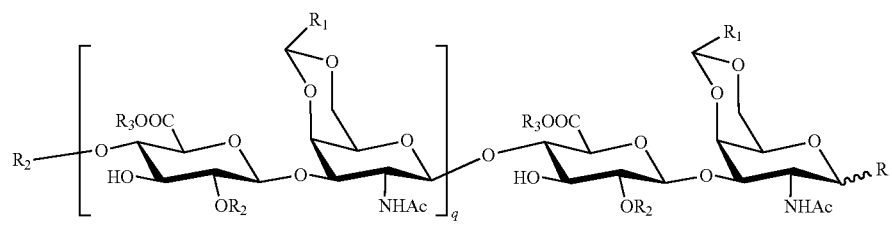

F

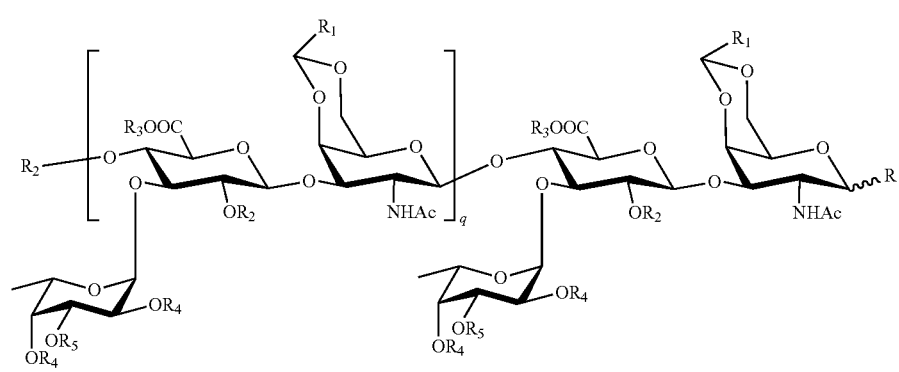

H

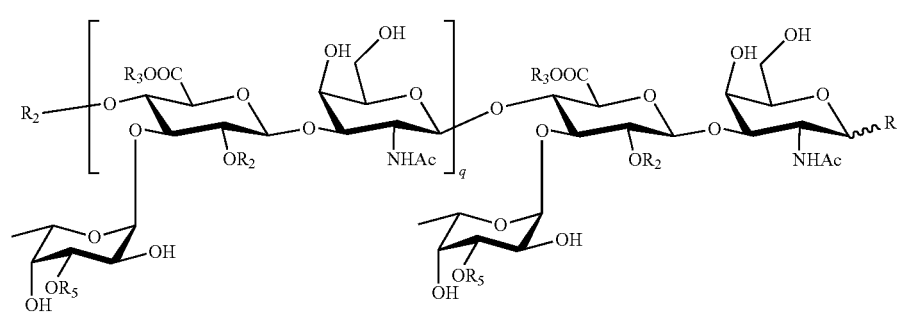

I

Definition of each substituent is as defined in the above synthesis method. Preferably, when R is azido, phenoxy, C1-C4 alkylthio, C1-C4 alkanoylthio, benzoyloxy, or benzoylthio, ∿∿ is in β configuration; and when R is C1-C4 alkoxy, ∿∿ is in a configuration.

In a particularly preferred embodiment of the present application, the present application provides intermediate compounds for preparing the above key intermediate. The intermediate compound is selected from:

azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)] disodium salt;

azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)] trisodium salt;

azido[(β-D-glucopyranosyluronic acid)-(1→3)-(4,6-O-benzylidene-2-deoxy-2-N-acetamido-β-D-galactopyranosyl)-(1→4)-(β-D-g lucopyranosyluronic acid)-(1→3)-(4,6-O-benzylidene-2-deoxy-2-N-acetamido-β-D-galactopyranosyl)] disodium salt;

azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)] trisodium salt;

azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)];

azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)];

azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]};

azido{(2,4-di-O-p-methoxybenzyl-3-O-acetylpropionyl-α-L-fucosyl)-(1→3)-(2,4-di-O-benzoyl-3-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]};

azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]};

azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]};

methyl-[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-α-D-galactopyranosyl)] disodium salt;

methyl-[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-α-D-galactopyranosyl)] disodium salt;

methyl-[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-α-D-galactopyranosyl)];

methyl-{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-α-D-galactopyranosyl)]}; and methyl-{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-α-D-galactopyranosyl]}.

In a fourth aspect, the present application provides a pharmaceutical composition including the fucosylated chondroitin sulfate oligosaccharide described above. The above pharmaceutical composition provided in the present application may be in a form for oral or parenteral administration. The dosage may be 0.1-1000 mg/time/day.

In a fifth aspect, the present application provides use of the fucosylated chondroitin sulfate oligosaccharide described above in the preparation of an anticoagulant medicament. The fucosylated chondroitin sulfate oligosaccharide compound provided by the present application possesses good anticoagulant activity, can significantly prolong activated partial thrombin time (APTT), and has no significant influence on prothrombin time (PT) and thrombin time (TT).

In the present application, the fucosylated chondroitin sulfate oligosaccharide is obtained by using chondroitin sulfate polysaccharide, which is easy to produce and extract, as a raw material, and hydrolyzing the raw material with inexpensive hyaluronidase of an animal testis origin to obtain oligosaccharide fragments which are convenient for chemical modification, and then performing conventional procedures of group protection and glycosylation. The whole route is simple and highly effective, and there are groups that can be labeled (for example, the azide group, which is convenient for labeling by click reaction at later stage), which provides a support for the biological function exploration and medicinal chemical research of the fucosylated chondroitin sulfate.

Other features and advantages of the application will be set forth in the description which follows, and in part will be apparent from the description, or may be learned by practice of the present application. The objects and other advantages of the present application can be realized and obtained by solutions specified in the description and claims.

DETAILED DESCRIPTION

In order to make the purpose, technical solution and advantages of the present application clearer, description of Examples of the present application will be made in detail below. It should be noted that the Examples in the present application and the features in the Examples may be arbitrarily combined with each other provided that there is no conflict.

The implementation of the present application is further illustrated by the following Examples, which is not intended to limit the protection scope of the present application.

Detection Instruments:
  Nuclear magnetic resonance: Bruker AV-400 nuclear magnetic resonance spectrometer.
  Mass spectrometry: Bruker APEX IV mass spectrometer.
Abbreviations:
  $CDCl_3$ is deuterated chloroform
  EtOAc is ethyl acetate
  MeOH is methanol
  HRMS: High resolution mass spectrometry
  ESI: Electrospray ionization mass spectrometry

Example 1: Synthesis of Chondroitin Polysaccharide 25 g of commercial chondroitin sulfate A sodium salt was added into 2.5 L hydrochloric acid-methanol solution (0.5% acetyl chloride, v/v), and stirred at room temperature for 24 hours. The solvent was removed by filtration with suction, and the resultant solid was added again into 2.5 L hydrochloric acid-methanol solution of the same concentration. This operation was repeated that the solution was changed for three times. The final solid obtained was dissolved in 750 mL of sodium hydroxide solution with a concentration of 0.1 M, and stirred at room temperature for 24 hours. IR-120 cation exchange resin was added to neutralize the solution to pH=3.5. The resin was removed by filtration. A proper amount of sodium hydroxide solid was added to adjust the pH back to 8.0. Concentration was performed to dryness, to obtain a white syrup. The syrup was then dissolved with a small amount of distilled water and slowly dropped into 2000 mL of absolute ethanol with vigorous stirring and a white precipitate was obtained. The precipitate was collected by filtration under reduced pressure, and the filter cake was rinsed with a small amount of cold absolute ethanol. Then the solid collected was dried in a desiccator containing anhydrous calcium chloride under reduced pressure to constant weight and 15.0 g chondroitin polysaccharide was obtained as a white amorphous powdery solid. The crude product can be directly used in the next synthesis step without further purification.

Example 2: Synthesis of (β-D-glucopyranosyluronic acid)-(1→3)-(2-deoxy-N-acetamino-β-D-galactopyranosyl)-(1→4)-(β-D-glucopyranosyluronic acid)-(1→3)-2-deoxy-N-acetamino-D-galactopyranose disodium salt, (β-D-glucopyranosyluronic acid)-(1→3)-(2-deoxy-N-acetamido-β-D-galactopyranosyl)-(1→4)-(β-D-glucopyranosyluronic acid)-(1→3)-(2-deoxy-N-acetamido-β-D-galactopyranosyl)-(1→4)-(β-D-glucopyranosyluronic acid)-(1→3)-2-deoxy-N-acetamino-D-galactopyranose trisodium salt, and (β-D-glucopyranosyluronic acid)-(1→3)-(2-deoxy-N-acetamido-β-D-galactopyranosyl)-(1→4)-(β-D-glucopyranosyluronic acid)-(1→3)-(2-deoxy-N-acetamino-β-D-galactopyranosyl)-(1→4)-(β-D-glucopyranosyluronic acid)-(1→3)-(2-deoxy-N-acetamido-β-D-galactopyranosyl)-(1→4)-(β-D-glucopyranosyluronic acid)-(1→3)-(2-deoxy-N-acetamido-β-D-galactopyranose tetrasodium salt 15.0 g of chondroitin polysaccharide obtained in Example 1 was added into 750 mL of 0.10 M sodium acetate-acetic acid buffer containing 0.15 M sodium chloride with a pH of 5.00. Temperature of the reaction solution was raised to 37.0° C. by thermostatic water bath, 375 mg of hyaluronidase dry powder (purchased from Sigma-Aldrich, Catalog number H-3506, Lot #SLBL1922V) was added and stirred at 37° C. for 7 days. At the end of the reaction, the reaction solution was heated to boil and stirred at 105° C. for 15 min. After the solution was no longer cloudy, it was quickly cooled to room temperature, mixed with 1/20 volume of absolute ethanol, then distilled under reduced pressure, and concentrated to dryness, to obtain a white syrup. The syrup was then dissolved with a small amount of distilled water and slowly dropped into 2000 mL of absolute ethanol with vigorous stirring, and a white precipitate was obtained. The precipitate was collected by filtration under reduced pressure, and filter cake was rinsed with a small amount of cold absolute ethanol. Then the solid collected was dried in a desiccator containing anhydrous calcium chloride under reduced pressure to constant weight and 22 g of a white amorphous powdery solid was obtained.

5.0 g crude product was first desalted using Sephadex LH-20, and then separated with strong anion type exchange resin, and eluted using NaCl solution (0.15 M~0.20 M). Fractions were monitored by TLC (n-butanol/water/ethanol/acetic acid=1/1/1/0.05), and then desalted using Sephadex LH-20, and lyophilized respectively to obtain the target tetrasaccharide i.e., (β-D-glucopyranosyluronic acid)-(1→3)-(2-deoxy-N-acetamino-β-D-galactopyranosyl)-(1→4)-(β-D-glucopyranosyluronic acid)-(1→3)-2-deoxy-N-acetamino-D-galactopyranose disodium salt (1.26 g, 38%), hexasaccharide i.e., (β-D-glucopyranosyluronic acid)-(1→3)-(2-deoxy-N-acetamido-β-D-galactopyranosyl)-(1→4)-(β-D-glucopyranosyluronic acid)-(1→3)-(2-deoxy-N-acetamido-β-D-galactopyranosyl)-(1→4)-(β-D-glucopyranosyluronic acid)-(1→3)-2-deoxy-N-acetamino-D-galactopyranose trisodium salt (1.15 g, 35%), and octasaccharide i.e., (β-D-glucopyranosyluronic acid)-(1→3)-(2-deoxy-N-acetamino-β-D-galactopyranosyl)-(1→4)-(β-D-glucopyranosyluronic acid)-(1→3)-(2-deoxy-N-acetamino-β-D-galactopyranosyl)-(1→4)-(β-D-glucopyranosyluronic acid)-(1→3)-(2-deoxy-N-acetamido-β-D-galactopyranosyl)-(1→4)-(β-D-glucopyranosyluronic acid)-(1→3)-2-deoxy-N-acetamino-D-galactopyranose tetrasodium salt (427 mg, 13%).

Spectral data of target oligosaccharides are consistent with those reported in literature. The tetrasaccharide: $R_f$=0.30 (n-butanol/water/ethanol/acetic acid=1/1/1/0.05); ESI-Q-TOF (negative ion mode) calculated value: $[M-2Na]^{2-}$ m/z 387.1095, measured value: 387.1082; the hexasaccharide: $R_f$=0.24 (n-butanol/water/ethanol/acetic acid=1/1/1/0.05); ESI-Q-TOF (negative ion mode) calculated value: $[M-3Na+H]^{2-}$ m/z 576.6652, measured value 576.6622; the octasaccharide: $R_f$=0.20 (n-butanol/water/ethanol/acetic acid=1/1/1/0.05); ESI-Q-TOF (negative ion mode) calculated value: $[M-4Na+2H]^{2-}$ m/z 766.2209, measured value: 766.2228.

Example 3: Synthesis of azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)] disodium salt (β-D-glucopyranosyluronic acid)-(1→3)-(2-deoxy-N-acetamino-β-D-galactopyranosyl)-(1→4)-(β-D-glucopyranosyluronic acid)-(1→3)-2-deoxy-N-acetamino-D-galactopyranosyl disodium salt (660 mg, 0.81 mmol), N-methylmorpholine (2.4 mL, 24.0 mmol), and sodium azide (3.0 g, 46.0 mmol) were dissolved in water (15 mL) and cooled to 0° C. 2-chloro-1,3-dimethylimidazolinium chloride (1.4 g, 8.4 mmol) was added and stirred for 15 min, and then the ice bath was removed. Temperature was raised naturally to room temperature, and the reaction was continued for 36 hours. After the reaction was completed, the solvent was removed by concentration, followed by desalting using Sephadex LH-20 and lyophilization, and a white solid (531 mg, 78%) was obtained. $R_f$=0.24 (n-butanol/water/ethanol/acetic acid=1/1/1/0.05); $^1$H NMR (600 MHz, $D_2O$) δ 4.75 (1H, d, J=9.4 Hz), 4.54-4.50 (3H, m), 4.19 (2H, m), 4.07-4.01 (2H, m), 3.89 (1H, dd, J=3.1 Hz, J=10.7 Hz), 3.84-3.76 (7H, m), 3.73-3.70 (3H, m), 3.62-3.59 (1H, m), 3.52-3.49 (2H, m), 3.42-3.37 (1H, m), 3.36-3.32 (1H, m), 2.06 (3H, s), 2.05 (3H, s); $^{13}$C NMR (150 MHz, $D_2O$) δ 175.9, 175.0, 174.9, 174.5, 104.2, 104.1, 100.9, 88.9, 80.3, 79.9, 79.7, 77.0, 76.4, 76.1, 75.3, 75.0, 73.7, 72.7, 72.4, 71.8, 67.7, 61.1, 61.0, 51.0, 50.4, 22.5, 22.2; ESI-Q-TOF (negative ion mode), calculated value: [M~2Na]$^{2-}$ m/z 399.6127, measured value: 399.6119.

Example 4: Synthesis of azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)] trisodium salt (β-D-glucopyranosyluronic acid)-(1→3)-(2-deoxy-N-acetamido-β-D-galactopyranosyl)-(1→4)-(β-D-glucopyranosyluronic acid)-(1→3)-(2-deoxy-N-acetamido-β-D-galactopyranosyl)-(1→4)-(β-D-glucopyranosyluronic acid)-(1→3)-2-deoxy-N-acetamino-D-galactopyranose trisodium salt (500 mg, 0.41 mmol), N-methylmorpholine (1.2 mL, 12.0 mmol), and sodium azide (1.5 g, 23.0 mmol) were dissolved in water (10 mL) and cooled to 0° C. 2-chloro-1,3-dimethylimidazolinium chloride (0.7 g, 4.2 mmol) was added and stirred for 15 min, and then the ice bath was removed. Temperature was raised naturally to room temperature, and the reaction was continued for 36 hours. After the reaction was completed, the solvent was removed by concentration, followed by desalting using Sephadex LH-20 and lyophilization, and a white solid (383 mg, 75%) was obtained. $R_f$=0.30 (n-butanol/water/ethanol/acetic acid=1/1/1/0.05); $^1$H NMR (600 MHz, $D_2O$) δ 4.75 (1H, d, J=9.5 Hz), 4.54-4.50 (4H, m), 4.19 (1H, m), 4.15-4.13 (1H, m), 4.07-4.00 (3H, m), 3.91-3.88 (1H, dd, J=2.8 Hz, J=10.7 Hz), 3.84-3.75 (10H, m), 3.72-3.70 (5H, m), 3.62-3.58 (2H, m), 3.54-3.49 (3H, m), 3.42-3.33 (4H, m), 2.06 (3H, s), 2.05 (3H, s), 2.04 (3H, s); $^{13}$C NMR (150 MHz, $D_2O$) δ 175.9, 175.0, 174.6, 174.5, 104.3, 104.2, 104.1, 100.8, 88.9, 80.3, 79.9, 79.7, 77.0, 76.4, 76.1, 75.3, 75.0, 73.7, 72.7, 72.5, 72.4, 71.8, 67.7, 61.1, 61.0, 51.0, 50.9, 50.4, 22.5, 22.2; ESI-Q-TOF (negative ion mode), calculated value: [M~3Na+H]$^{2-}$ m/z 589.1684, measured value: 589.1676.

Example 5: Synthesis of azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)] disodium salt Azido[(β-D-glucopyranosyluronic acid)-(1→3)-(2-deoxy-2-N-acetamino-β-D-galactopyranosyl)-(1→4)-(β-D-glucopyranosyluronic acid)-(1→3)-(2-deoxy-2-N-acetamino-β-D-galactopyranosyl)] disodium salt (540 mg, 0.64 mmol) and camphorsulfonic acid (300 mg, 1.29 mmol) were dissolved in anhydrous N, N-dimethylformamide (10 mL) under the protection of Argon. Benzaldehyde dimethyl acetal (1.5 mL, 9.6 mmol) was added, heated to 45° C. and allowed tp react under reduced pressure for 5 hours. After the reaction was completed with monitoring by TLC, saturated sodium bicarbonate solution was added dropwise for quenching, and the reaction solution was directly purified by Sephadex LH-20 (eluted with pure water) followed by lyophilization, and a white solid (556 mg, 85%) was obtained. $R_f$=0.50 ($CHCl_3$/MeOH/$H_2O$/=1/1/0.3); $^1$H NMR (600 MHz, $D_2O$) δ 7.61-7.57, 7.50-7.48 (10H, m), 5.80 (1H, s, PhCH), 5.76 (1H, s, PhCH), 4.89 (1H, d, J=9.3 Hz), 4.66 (1H, d, J=8.5 Hz), 4.62 (1H, m), 4.61 (1H, m), 4.55 (1H, d, J=7.9 Hz), 4.52 (1H, d, J=7.9 Hz), 4.29-4.23 (4H, m), 4.21-4.17 (2H, m), 4.09 (1H, dd, J=3.2 Hz, J=10.9 Hz), 4.02 (1H, dd, J=3.3 Hz, J=11.0 Hz), 3.88 (1H, m), 3.79 (1H, m), 3.77-3.72 (2H, m), 3.71-3.69 (1H, m), 3.62 (1H, dd, J=J=9.2 Hz), 3.51-3.46 (2H, m), 3.35-3.25 (2H, m), 2.06 (3H, s, $CH_3CO$), 2.04 (3H, s, $CH_3CO$); $^{13}$C NMR (150 MHz, $D_2O$) δ 175.8, 175.1, 175.0, 174.2, 173.3, 167.6, 136.6, 136.5, 129.9, 129.8, 128.6, 126.5, 126.4, 104.4, 104.3, 101.3, 101.1, 88.7, 80.4, 77.6, 76.6, 76.2, 75.3, 75.2, 74.9, 73.5, 72.5, 72.1, 71.7, 68.9, 68.6, 68.1, 66.4, 50.8, 50.1, 45.4, 38.8, 34.2, 22.6, 22.2; ESI-Q-TOF (negative ion mode), calculated value: $C_{42}H_{49}N_5O_{22}^{2-}$ m/z 487.6440, measured value: 487.6438.

Example 6: Synthesis of azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)] trisodium salt Azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)] trisodium salt (450 mg, 0.36 mmol) and camphorsulfonic acid (345 mg, 1.50 mmol) were dissolved in anhydrous N, N-dimethylformamide (7.5 mL) under the protection of Argon. Benzaldehyde dimethyl acetal (1.35 mL, 9.0 mmol) was added, heated to 45° C. and allowed to react under reduced pressure for 5 hours. After the reaction was completed with monitoring by TLC, saturated sodium bicarbonate solution was added dropwise for quenching, and the reaction solution was directly purified by Sephadex LH-20 (eluted with pure water) followed by lyophilization, and a white solid (445 mg, 81%) was obtained. $R_f$=0.45 ($CHCl_3$/MeOH/$H_2O$/=1/1/0.3); $^1$H NMR (600 MHz, $D_2O$) δ 7.61-7.57, 7.50-7.48 (15H, m), 5.79 (1H, s, PhCH), 5.75 (2H, s, PhCH), 4.88 (1H, d, J=9.3 Hz), 4.67-4.64 (2H, m), 4.62 (1H, m), 4.59 (1H, m), 4.57-4.51 (4H, m), 4.27-4.22 (6H, m), 4.22-4.15 (3H, m), 4.08 (1H, dd, J=3.2 Hz, J=11.0 Hz), 4.03-4.00 (2H, m), 3.86 (1H, m), 3.78-3.69 (7H, m), 3.64-3.60 (2H, m), 3.51-3.48 (2H, m), 3.35-3.28 (3H, m), 2.06 (3H, s, $CH_3CO$), 2.05 (3H, s, $CH_3CO$), 2.04 (3H, s, $CH_3CO$); $^{13}$C NMR (150 MHz, $D_2O$) δ 175.7, 175.1, 175.0, 174.2, 167.7, 136.7, 136.6, 129.9, 129.8, 128.7, 128.6, 126.6, 126.5, 104.5, 104.4, 101.3, 101.1, 88.7, 80.5, 78.0, 77.6, 76.7, 76.2, 75.3, 75.2, 75.0, 73.6, 72.5, 72.1, 71.7, 69.0, 68.6, 68.2, 66.4, 65.6, 57.0, 50.8, 50.1, 22.6, 22.2; ESI-Q-TOF (negative ion mode), calculated value: $C_{63}H_{73}N_6O_{33}{}^{3-}$ m/z 480.4745, measured value: 480.4741.

Example 7: Synthesis of azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzylidene-β-D-methyl glucopyranosyluronate)-(1→3)-(4,6-O-benzylidene-2-deoxy-2-N-acetamido-β-D-galactopyranosyl)]

Azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)] disodium salt (170 mg, 0.166 mmol), and benzoic anhydride (1.17 g, 5.17 mmol) were dissolved in anhydrous N, N-dimethylformamide (7.5 mL), heated at 85° C. for 7 hours, and cooled to room temperature. Anhydrous pyridine (4 mL) and 4-dimethylaminopyridine (41 mg, 0.335 mmol) were added, and allowed to react at ambient temperature for 36 hours. After the reaction was completed with monitoring by TLC, methanol (4 mL) and anhydrous sodium acetate (20 mg, 0.24 mmol) were added sequentially, and left to react overnight at room temperature. The reaction solution was concentrated to remove methanol. A large amount of anhydrous ether was added and a white and yellowish solid precipitated out. The filtrate was removed by filtration, and purification was performed by column chromatography ($CH_2Cl_2$/MeOH 30:1) to obtain a white solid (144 mg, and two-step yield 66%). $R_f$=0.35 ($CH_2Cl_2$/MeOH=20:1); $^1$H NMR (600 MHz, DMSO-$d_6$) δ 7.99-7.93, 7.69-7.60, 7.56-7.48, 7.44-7.43, 7.38-7.36, 7.31-7.29 (27H, m), 5.82 (1H, d, J=6.4 Hz), 5.43 (1H, s, PhCH), 5.37 (1H, s, PhCH), 5.09 (1H, m), 5.04 (1H, dd, J=J=9.6 Hz), 4.99 (1H, dd, J=J=8.0 Hz), 4.97-4.95 (2H, m), 4.84 (1H, dd, J=J=8.5 Hz), 4.56 (1H, d, J=7.4 Hz), 4.44 (1H, d, J=8.0 Hz), 4.41 (1H, d, J=9.9 Hz), 4.35 (1H, m), 4.27 (1H, m), 4.10-3.97 (6H, m), 3.93 (1H, m), 3.85 (2H, m), 3.80-3.76 (2H, m), 3.72 (1H, m), 3.68 (1H, m), 3.63 (3H, s, $COOCH_3$), 3.57 (1H, m), 3.48 (3H, s, $COOCH_3$), 1.17 (3H, s, $CH_3CO$), 1.15 (3H, s, $CH_3CO$); $^{13}$C NMR (150 MHz, DMSO-$d_6$) δ 169.0, 168.7, 167.8, 167.3, 165.1, 164.3, 138.3, 138.2, 133.6, 133.2, 132.8, 130.7, 129.7, 129.6, 129.5, 129.4, 129.2, 128.8, 128.7, 128.6, 128.5, 128.4, 128.0, 127.9, 126.1, 126.0, 101.0, 100.6, 100.0, 99.8, 88.2, 79.5, 77.9, 74.3, 73.6, 73.2, 72.3, 72.0, 71.4, 71.3, 68.3, 67.5, 65.9, 52.3, 52.2, 49.9, 48.9, 22.1, 21.9; ESI-Q-TOF (positive ion mode), calculated value: $C_{65}H_{71}N_6O_{25}{}^+$ m/z 1335.4463, measured value: 1335.8818.

Example 8: Synthesis of azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzylidene-β-D-methyl glucopyranosyluronate)-(1→3)-(4,6-O-benzylidene-2-deoxy-2-N-acetamido-β-D-galactopyranosyl)]

Azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)-(1→4)-(β-D-g lucopyranosyluronic acid)-(1→3)-(4,6-O-benzylidene-2-deoxy-2-N-acetamido-β-D-galactopyranosyl)] trisodium salt (350 mg, 0.231 mmol), and benzoic anhydride (1.62 g, 7.26 mmol) were dissolved in anhydrous N, N-dimethylformamide (15 mL), heated at 85° C. for 12 hours, and cooled to room temperature. Anhydrous pyridine (4 mL) and 4-dimethylaminopyridine (56 mg, 0.462 mmol) were added, and allowed to react at ambient temperature for 36 hours. After the reaction was completed with monitoring by TLC, methanol (4 mL) and anhydrous sodium acetate (28 mg, 0.346 mmol) were added sequentially, and left to react overnight at room temperature. The reaction solution was concentrated to remove methanol. A large amount of anhydrous ether was added and a white and yellowish solid precipitated out. The filtrate was removed by filtration and purification was performed by column chromatography ($CH_2Cl_2$/MeOH 20:1) to obtain a white solid (262 mg, and two-step yield 60%). $R_f$=0.28 ($CH_2Cl_2$/MeOH=20:1); $^1$H NMR (600 MHz, DMSO-$d_6$) δ 8.01-7.95, 7.71-7.62, 7.58-7.50, 7.46-7.45, 7.41-7.36, 7.33-7.27 (38H, m), 5.84 (1H, d, J=6.6 Hz), 5.45 (1H, s, PhCH), 5.38 (1H, s, PhCH), 5.34 (1H, s, PhCH), 5.08-5.03 (3H, m), 5.02-4.95 (4H, m), 4.87-4.83 (2H, m), 4.57 (1H, d, J=6.8 Hz), 4.52 (1H, d, J=6.6 Hz), 4.46 (1H, d, J=7.8 Hz), 4.43 (1H, d, J=10.0 Hz), 4.38 (1H, m), 4.28 (1H, m), 4.25 (1H, m), 4.12-3.98 (10H, m), 3.86 (3H, m), 3.80-3.78 (4H, m), 3.76-3.69 (3H, m), 3.63 (3H, s, $COOCH_3$), 3.61 (3H, s, $COOCH_3$), 3.59 (1H, m), 3.57 (1H, m), 3.51 (3H, s, $COOCH_3$), 1.19 (3H, s, $CH_3CO$), 1.16 (6H, s, $CH_3CO$); $^{13}$C NMR (150 MHz, DMSO-$d_6$) δ 168.9, 168.7, 168.6, 167.8, 167.3, 165.1, 164.4, 164.3, 138.3, 138.2, 133.6, 133.2, 132.8, 130.7, 129.7, 129.6, 129.5, 129.4, 129.2, 128.8, 128.7, 128.6, 128.5, 128.4, 128.0, 127.9, 126.1, 126.0, 101.0, 100.8, 100.7, 100.0, 99.8, 99.7, 88.2, 79.5, 79.4, 77.8, 74.3, 74.0, 73.6, 73.2, 72.3, 72.1, 72.0, 71.4, 71.3, 68.3, 67.5, 65.9, 52.3, 52.2, 34.7, 22.1, 21.9; ESI-Q-TOF (positive ion mode), calculated value: $C_{94}H_{106}N_8O_{37}{}^{2+}$ m/z 969.8341, measured value: 969.8078.

Example 9: Synthesis of azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]}

Azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)] (55.0 mg, 41.8 μmol), and ethyl-2,4-di-O-p-methoxybenzyl-3-O-acetylpropionyl-1-thio-β-L-fucose (137 mg, 0.251 mmol) were dissolved in anhydrous dichloromethane/N,N-dimethylformamide (1.8 mL/0.6 mL) under the protection of Argon. 4 Å molecular sieve (200 mg) was added, stirred at room temperature for 2 hours, and cooled to 0° C. N-iodosuccinimide (75.2 mg, 0.334 mmol) and silver trifluoromethanesulfonate (10.7 mg, 0.042 mmol) were added sequentially, and the temperature was kept constant for the reaction to continue for 2.5 hours. Temperature was slowly raised to room temperature, and reaction was left overnight. The reaction was quenched by adding triethylamine, and filtered using diatomite to remove the molecular sieve. Filtrate was evaporated to dryness, and the resultant solid was dissolved in mixed solvent of acetic acid/acetic anhydride (0.8 mL/2.4 mL), and allowed to react for 3 hours at 70° C. Solvent was dried with toluene, separation was performed by column chromatography (DCM/MeOH=35:1), and concentration was performed under reduced pressure, and a white solid (67.2 mg, 70%) was obtained. $R_f$=0.30 (DCM/MeOH=25:1), ESI-Q-TOF (positive ion mode), calculated value: $C_{119}H_{139}N_7O_{41}^{2+}$ m/z 1161.4515, measured value: 1161.4293.

Example 10: Synthesis of azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]}

Azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)] (71.4 mg, 37.5 μmol), and ethyl-2,4-di-O-p-methoxybenzyl-3-O-acetylpropionyl-1-thio-f3-L-fucose (217 mg, 0.375 mmol) were dissolved in anhydrous dichloromethane/N,N-dimethylformamide (2.2 mL/1.1 mL) under the protection of Argon. 4 Å molecular sieve (300 mg) was added, stirred at room temperature for 2 hours, and cooled to 0° C. N-iodosuccinimide (110 mg, 0.488 mmol) and silver trifluoromethanesulfonate (14.5 mg, 0.056 mmol) were added sequentially, and the temperature was kept constant for the reaction to continue for 2.5 hours. Temperature was slowly raised to room temperature, and reaction was left overnight. The reaction was quenched by adding triethylamine, and filtered using diatomite to remove the molecular sieve. Filtrate was evaporated to dryness, and the resultant solid was dissolved in mixed solvent of acetic acid/acetic anhydride (0.8 mL/2.4 mL), and allowed to react for 3 hours at 70° C. Solvent was dried with toluene, separation was performed by column chromatography (DCM/MeOH=35:1), and concentration was performed under reduced pressure, and a white solid (78.1 mg, 62%) was obtained. $R_f$=0.30 (DCM/MeOH=20:1), ESI-Q-TOF (positive ion mode), calculated value: $C_{175}H_{202}N_8O_{61}^{2+}$ m/z 1696.6503, measured value: 1696.6086.

Example 11: Synthesis of azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-1(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]}

Azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]} (46.0 mg, 0.02 mmol) was dissolved in a mixed solvent of dichloromethane (2 mL) and water (200 μL), and 2,3-dichloro-5,6-dicyano-p-benzoquinone (46 mg, 0.20 mmol) was added to react at room temperature for 4 hours. After the reaction was completed with monitoring by TLC, the reaction solution was diluted with dichloromethane, and the organic phase was washed with saturated sodium bicarbonate/sodium thiosulfate solution (1:1) and brine sequentially, and then stripped with dichloromethane for three times. Organic phases were combined, dried with anhydrous sodium sulfate, and the crude product obtained by concentration was dissolved in 80% acetic acid aqueous solution (2.0 mL), and reacted at 60° C. for 3 hours, and then dried with anhydrous toluene, purified by Sephadex LH-20 with dichloromethane/methanol (1:1) used directly as an eluent, and concentrated under reduced pressure, and white solid was obtained (24.0 mg, two-step yield 73%). $R_f$=0.20 (DCM/MeOH 8:1); ESI-Q-TOF (positive ion mode), calculated value: $C_{73}H_{95}N_6NaO_{37}^{2+}$ m/z 835.2812, measured value: 835.2966.

Example 12: Synthesis of azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]}

Azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]-(1→4)-[(2,4-di-O-p-methoxybenzyl-3-O-acetylpropion yl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]} (35.7 mg, 0.011 mmol) was dissolved in a mixed solvent of dichloromethane (1.5 mL) and water (150 μL), and 2,3-dichloro-5,6-dicyano-p-benzoquinone (37 mg, 0.165 mmol) was added to react at room temperature for 4 hours. After the reaction was completed with monitoring by TLC, the reaction solution was diluted with dichloromethane, and the organic phase was washed with saturated sodium bicarbonate/sodium thiosulfate solution (1:1) and brine sequentially, and then stripped with dichloromethane for three times. Organic phases were combined, dried with anhydrous sodium sulfate, and the crude product obtained by concentration was dissolved in 80% acetic acid aqueous solution (2.0 mL), and reacted at 60° C. for 3 hours, and then dried with anhydrous toluene, purified by Sephadex LH-20 with dichloromethane/methanol (1:1) used directly as an eluent, and concentrated under reduced pressure, and a white solid was obtained (17.8 mg, two-step yield 71%). $R_f$=0.30

(DCM/MeOH 6:1); ESI-Q-TOF (positive ion mode), calculated value: $C_{106}H_{134}N_6Na_2O_{55}^{2+}$ m/z 1208.3829, measured value: 1208.4847.

Example 13: Synthesis of azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]} decasodium salt Under the protection of Argon, azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]} (24 mg, 14.7 μmol) was dissolved in anhydrous N, N-dimethylformamide (1.0 mL). Sulfur trioxide trimethylamine complex (246 mg, 1.77 mmol) was added to react for 90 hours at 50° C., and cooled to room temperature. The reaction was quenched by adding triethylamine (100 μL) and methanol (150 μL) sequentially, purified by Sephadex LH-20 with dichloromethane/methanol 1:1 used directly as eluent, and concentrated under reduced pressure to obtain a white solid. The white solid was dissolved in mixed solvent of tetrahydrofuran-water (3:1, 2 mL), cooled to −5° C., and a newly made 1 M lithium hydroxide-35% hydrogen peroxide (2:1, 0.75 mL) mixed solution was added dropwise. The reaction was performed at −5° C. for 1 hour, and then continued overnight at room temperature. Methanol (0.5 mL) was added in the condition of ice bath, and 4 M sodium hydroxide solution (1.3 mL) was slowly added dropwise. The temperature was raised naturally to room temperature, and the reaction was performed for 10 hours. The reaction solution was neutralized with IR-120 cation exchange resin to pH=7, filtered, and the resin was rinsed with distilled water. The filtrate was concentrated, purified using Sephadex LH-20 with water used as eluent and lyophilized, and a white solid was obtained (22.0 mg, two-step yield 77%). ESI-Q-TOF (negative ion mode), calculated value: $C_{40}H_{67}N_7O_{54}S_8^{2-}$ m/z 882.5244, measured value: 882.5250.

Example 14: Synthesis of azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]} pentadecasodium salt Under the protection of Argon, azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)} (19.5 mg, 8.2 μmol) was dissolved in anhydrous N, N-dimethylformamide (0.8 mL). Sulfur trioxide trimethylamine complex (206 mg, 1.47 mmol) was added to react for 90 hours at 50° C., and cooled to room temperature. The reaction was quenched by adding triethylamine (100 μL) and methanol (150 μL) sequentially, purified by Sephadex LH-20 with dichloromethane/methanol 1:1 used directly as eluent, and concentrated under reduced pressure to obtain a white solid. The white solid was dissolved in mixed solvent of tetrahydrofuran-water (3:1, 2 mL), cooled to −5° C., and a newly made 1 M lithium hydroxide-35% hydrogen peroxide mixed solution (2:1, 0.75 mL) was added dropwise. The reaction was performed at −5° C. for 1 hour, and then continued overnight at room temperature. Methanol (0.5 mL) was added in the condition of ice bath, and 4 M sodium hydroxide solution (1.3 mL) was slowly added dropwise. The temperature was raised naturally to room temperature, and the reaction was performed for 10 hours. The reaction solution was neutralized with IR-120 cation exchange resin to pH=7, filtered, and the resin was rinsed with distilled water. The filtrate was concentrated, purified using Sephadex LH-20 with water used as eluent and lyophilized, and a white solid was obtained (16.2 mg, two-step yield 68%). ESI-Q-TOF (negative ion mode), calculated value: $C_{60}H_{100}N_9O_{81}S_{12}^{3-}$ m/z 875.3549, measured value: 875.3564.

Example 15: Synthesis of methyl-[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-α-D-galactopyranosyl) disodium salt (β-D-glucopyranosyluronic acid)-(1→3)-(2-deoxy-N-acetamino-β-D-galactopyranosyl)-(1→4)-(β-D-glucopyranosyluronic acid)-(1→3)-2-deoxy-N-acetamino-D-galactopyranose disodium salt (490 mg, 0.60 mmol) was dissolved in 50 mL hydrochloric acid-methanol solution (prepared by adding 3.5% by volume of acetyl chloride into anhydrous methanol), and was reacted for 16 hours at room temperature. 0.1 M sodium hydroxide solution was added dropwise with an ice bath to adjust pH of the solution to 12, and was stirred for 2 hours. Concentration was performed to remove the solvent, desalting was performed with Sephadex LH-20 followed by lyophilization, and a white solid was obtained (345 mg, 70%). $R_f$=0.24 (n-butanol/water/ethanol/acetic acid=1/1/1/0.05); $^1$H NMR (400 MHz, $D_2O$) δ 4.41-4.38 (3H, m), 4.32 (1H, d, J=8.5 Hz), 4.06 (1H, m), 4.01 (1H, m), 3.92-3.87 (2H, m), 3.72-3.62 (7H, m), 3.59-3.57 (4H, m), 3.49-3.45 (1H, m), 3.40-3.36 (5H, m), 3.28-3.19 (2H, m), 1.92 (3H, s), 1.90 (3H, s); $^{13}$C NMR (100 MHz, $D_2O$) δ 175.9, 175.0, 174.9, 174.5, 104.2, 104.1, 102.2, 100.9, 80.4, 80.2, 79.7, 76.1, 75.3, 75.0, 74.9, 73.7, 72.7, 72.5, 71.8, 67.8, 67.7, 61.1, 61.0, 57.1, 51.0, 22.6, 22.3; ESI-Q-TOF (negative ion mode), calculated value: $[M-2Na]^{2-}$ m/z 394.1173, measured value: 394.1180.

Example 16: Synthesis of methyl-[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-α-D-galactopyranosyl)] disodium salt Methyl-[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-α-D-galactopyranosyl)] disodium salt (195 mg) was used as raw material, and according to the synthesis method for azido[(β-D-glucopyranosyluronic acid)-(1→3)-(4,6-O-benzylidene-2-deoxy-2-N-acetamido-β-D-galactopyranosyl)-(1→4)-(β-D-glucopyranos yluronic acid)-(1→3)-(4,6-O-benzylidene-2-deoxy-2-N-acetamido-β-D-galactopyranosyl)] disodium salt, a white solid was prepared (200 mg, 84%). $R_f$=0.50 (CHCl$_3$/MeOH/H$_2$O/=1/1/0.3); ESI-Q-TOF (negative ion mode), calculated value: $C_{43}H_{52}N_5O_{23}{}^{2-}$ m/z 482.1486, measured value: 482.1473.

Example 17: Synthesis of methyl-[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-α-D-galactopyranosyl)]

Methyl-[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-α-D-galactopyranosyl)] disodium salt (200 mg) was used as raw material, and according to the synthesis method for azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)], a white solid was prepared (180 mg, two-step yield 70%). $R_f$=0.35 (CH$_2$Cl$_2$/MeOH=20:1); $^1$H NMR (400 MHz, DMSO-d$_6$) δ 8.24-8.01, 7.62-7.38, 7.34-7.32, 7.14 (25H, m), 6.21 (1H, m), 5.58-5.51 (2H, m), 5.47-5.46 (2H, m), 5.31 (1H, dd, J=J=9.6 Hz), 5.23 (1H, m), 5.08 (1H, m), 5.06 (1H, m), 4.96 (1H, d, J=8.6 Hz), 4.91 (1H, d, J=7.1 Hz), 4.77 (1H, m), 4.52 (1H, m), 4.47 (1H, m), 4.27-4.20 (3H, m), 4.13 (1H, m), 4.04-3.96 (3H, m), 3.90-3.86 (2H, m), 3.69 (3H, s, COOCH$_3$), 3.65 (3H, s, COOCH$_3$), 3.52 (1H, m), 3.40 (4H, m), 1.54 (3H, s, CH$_3$CO), 1.41 (3H, s, CH$_3$CO); ESI-Q-TOF (positive ion mode), calculated value: $C_{66}H_{74}N_3O_{26}{}^+$ [M+NH$_4{}^+$] m/z 1324.4555, measured value: 1324.4960.

Example 18: Synthesis of methyl-{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-α-D-galactopyranosyl)]}

Methyl-[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-α-D-galactopyranosyl)] (130 mg) was used as raw material, and according to the synthesis method for azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]}, a white solid was prepared (164.7 mg, 73%). $R_f$=0.30 (DCM/MeOH=25:1), ESI-Q-TOF (positive ion mode), calculated value: $C_{120}H_{142}N_4O_{42}{}^{2+}$ [M+2NH$_4$]$^{2+}$ m/z 1155.9561, measured value: 1155.5210.

Example 19: Synthesis of methyl-{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-α-D-galactopyranosyl)]}

Methyl-{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamido-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-α-D-galactopyranosyl)]} (140 mg) was used as raw material, and according to the synthesis method for azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-P-D-galactopyranosyl)]}, a white solid was prepared (68.6 mg, two-step yield 70%). $R_f$=0.20 (DCM/MeOH 8:1); ESI-Q-TOF (positive ion mode), calculated value: $C_{74}H_{102}N_4O_{38}{}^{2+}$ m/z 827.3081, measured value: 827.1324.

Example 20: Synthesis of methyl-{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-α-D-galactopyranosyl)]} decasodium salt Methyl-{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-α-D-galactopyranosyl)]} (68.6 mg) was used as raw material, and according to the synthesis method for azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]} decasodium salt, a white solid was prepared (64.0 mg, two-step yield 78%). $^1$H NMR (400 MHz, D$_2$O) δ 5.62 (1H, d, J=3.8 Hz), 5.52 (1H, d, J=3.7 Hz), 4.84 (1H, m), 4.80 (1H, m), 4.75 (2H, m), 4.62 (1H, m), 4.50-4.36 (7H, m), 4.25-4.06 (7H, m), 4.02-3.88 (7H, m), 3.70-3.52 (8H, m), 3.46 (3H, s, OCH$_3$), 1.99 (3H, s, COOCH$_3$), 1.95 (3H, s, COOCH$_3$), 1.29 (3H, d, J=6.4 Hz), 1.18 (3H, d, J=6.5 Hz); $^{13}$C NMR (100 MHz, D$_2$O) δ 175.0, 174.9, 103.7, 101.9, 99.9, 96.6, 81.5, 81.1, 80.9, 77.2, 76.5, 76.3, 76.1, 75.9, 75.4, 75.2, 75.1, 73.6, 72.9, 72.3, 71.8, 69.9, 68.0, 67.2, 66.5, 66.3, 66.2, 57.3, 51.4, 22.6, 22.3, 15.8, 15.7; ESI-Q-TOF (negative ion mode), calculated value: $C_{41}H_{67}N_3O_{55}S_8{}^{2-}$ m/z 868.5157, measured value: 868.5182.

Anticoagulant Activity Test

Oligosaccharide compounds of the present application, J1 (a compound of formula J, in which Y=Na, q=1, R is azido, and ∿ is in β configuration), J2 (a compound of formula J, in which Y=Na, q=2, R is azido, and ∿ is in β configuration), J3 (a compound of formula J, in which Y=Na, q=3, R is azido, and ∿ is in β configuration), and J4 (a compound of formula J, in which Y=Na, q=4, R is azido, and ∿ is in β configuration) were assayed for anticoagulant activity, including activated partial thrombin time (APTT), prothrombin time (PT) and thrombin time (TT).

APTT Assay

The whole experiment was carried out according to the instruction of the APTT kit. Firstly, 20 ul of platelet-poor plasma and 5 ul of the solution to be tested (control or sample solution) were mixed into a test cup and incubated in preheating zone at 37° C. for 3 min. Then 25 ul of APTT reagent was added to the mixed system, and then continued to incubate at 37° C. for 3 min. Next, the test cup was moved to the test zone, and 25 ul of calcium chloride solution preheated for 5 min was added. At the same time, recording of fibrin formation time was immediately initiated, and when the experiment was completed, the fibrin formation time was read from the coagulation analyzer.

PT Assay

The whole experiment was carried out according to the instruction of the PT kit. Firstly, 20 ul of platelet-poor plasma and 5 ul of the solution to be tested (control or sample solution) were mixed into a test cup and incubated in preheating zone at 37° C. for 3 min. Then the test cup was moved to the test zone, and 50 ul of preheated PT reagent was added (preheating time is longer than 10 min, but not more than 30 min). At the same time, recording of fibrin formation time was immediately initiated, and when the experiment was completed, the fibrin formation time was read from the coagulation analyzer.

TT Assay

The whole experiment was carried out according to the instruction of the TT kit. Firstly, 20 ul of platelet-poor plasma and 5 ul of the solution to be tested (control or sample solution) were mixed into a test cup and incubated in preheating zone at 37° C. for 3 min. Then the test cup was moved to the test zone, and 50 ul of preheated TT reagent was added (preheating time is longer than 10 min, but not more than 30 min). At the same time, recording of fibrin formation time was immediately initiated, and when the experiment was completed, the fibrin formation time was read from the coagulation analyzer.

Results of the assays are as follows (data in the table represent the concentration required to double APTT/PT/TT):

| Compound | APTT, µg/ml | PT, µg/ml | PT, µg/ml |
|---|---|---|---|
| J1 | 120.39 | >128 | >128 |
| J2 | 22.73 | >128 | >128 |
| J3 | 9.71 | >128 | >128 |
| J4 | 6.56 | >128 | >128 |
| Low molecular weight heparin (Enoxaparin sodium) | 11.61 | >128 | 4~8 |

Although the embodiments disclosed in the present application are as above, what is described is only for the convenience of understanding the embodiments adopted in the present application, and is not intended to limit the present application. Without departing from the spirit and scope disclosed in the present application, a person skilled in the art to which the present application pertains can make any modification and change to the implementation form and details, but the protection scope of the present application shall still be subjected to the scope defined in the appended claims.

The invention claimed is:

1. A fucosylated chondroitin sulfate oligosaccharide shown as Formula J, wherein:

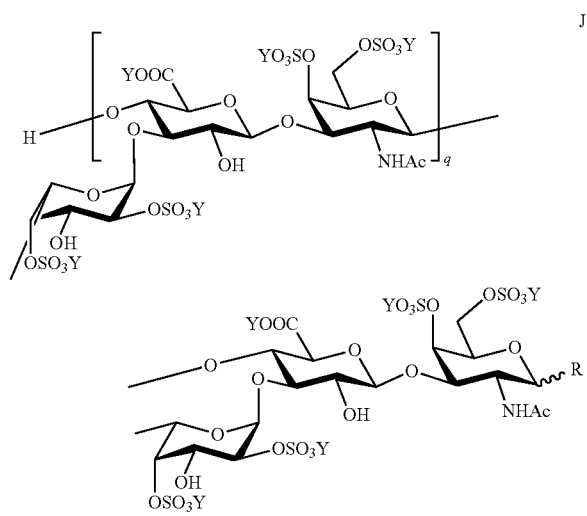

in Formula J, Ac is acetyl; q is a positive integer and q≤10; Y is H, alkali metal, alkaline earth metal, or $N(R_6)_4$, wherein $R_6$ is C1-C4 alkyl; R is azido, C1-C4 alkoxy, phenoxy, C1-C4 alkylthio, C1-C4 alkanoylthio, benzoyloxy or benzoylthio.

2. The fucosylated chondroitin sulfate oligosaccharide of claim 1, wherein when R is azido, phenoxy, C1-C4 alkylthio, C1-C4 alkanoylthio, benzoyloxy, or benzoylthio, ∿ is in β configuration; and when R is C1-C4 alkoxy, ∿ is in α configuration.

3. A pharmaceutical composition comprising the fucosylated chondroitin sulfate oligosaccharide of claim 2.

4. The fucosylated chondroitin sulfate oligosaccharide of claim 1, wherein in Formula J, q is 1, 2, 3, or 4; Y is H, sodium, lithium, potassium, calcium or magnesium.

5. A pharmaceutical composition comprising the fucosylated chondroitin sulfate oligosaccharide of claim 4.

6. The fucosylated chondroitin sulfate oligosaccharide of claim 1, selected from one of the following compounds:
azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-β-D-galactopyranosyl)]} decasodium salt;
azido{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-β-D-glucopyranosyluronic acid)-(1→3)-(4,6-di-O-sulfo-2-deoxy-2-N-acetamido-β-D-galactopyranosyl)-(1→4)-[(2,4-di-O-sulfo-α-L-fucosyl)-(1→3)-(β-D- glucopyranosyluronic acid)-(1→3)-(4,6-di-O-sulfo-2-deoxy-2-N-acetamido-β-D-galactopyranosyl)]} pentadecasodium salt; and methyl-{(2,4-di-O-sulfo-α-L-fucosyl)-(1→3)-(β-D-glucopyranosyluronic acid)-(1→3)-(4,6-di-O-sulfo-2-deoxy-2-N-acetamino-β-D-galactopyranosyl)-(1→4)-[(2,4-di-O-sulfo-α-L-fucosyl)-(1→3)-(β-D-glucopyranosyluronic acid)-(1→3)-(4,6-di-O-sulfo-2-deoxy-2-N-acetamido-α-D-galactopyranosyl)]} decasodium salt.

7. A pharmaceutical composition comprising the fucosylated chondroitin sulfate oligosaccharide of claim 6.

8. A synthesis method of the fucosylated chondroitin sulfate oligosaccharide of claim 1, comprising the following steps:

(1) removing the sulfonate group from a compound of Formula A in a C1-C4 alkanol solution of an inorganic acid, and treating with MOH base, to obtain a compound of Formula B; wherein m in Formula A and n in Formula B are positive integers, and 20≤n≤m;

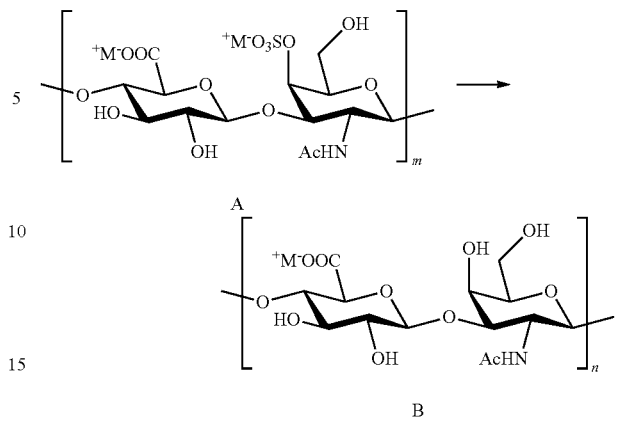

(2) subjecting the compound of Formula B in a weakly acidic buffer solution containing sodium chloride, and by the activity of hyaluronidase, to obtain a compound of Formula C; wherein the hyaluronidase is originated from animal testis selected from bovine testis or sheep testis; q is a positive integer from 1-10;

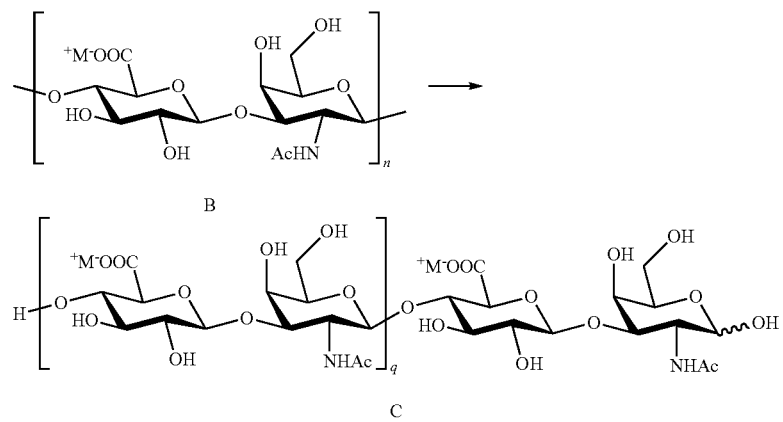

(3) subjecting the compound of Formula C to react with a nucleophilic reagent RX, to obtain a compound of Formula D;

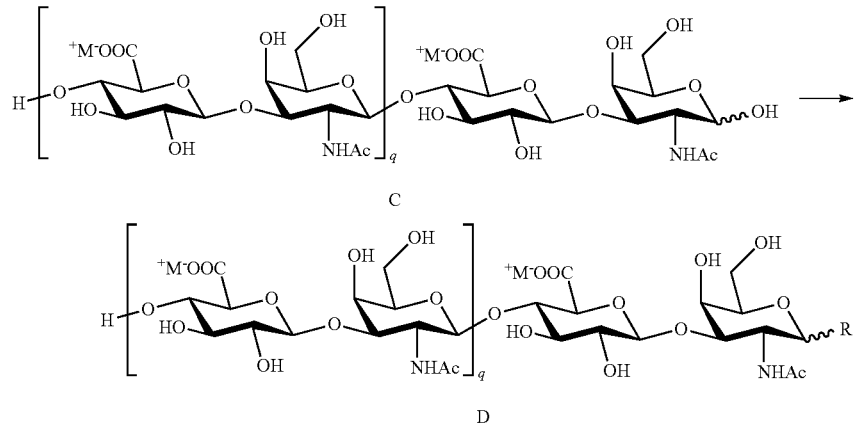

(4) subjecting the compound of Formula D to selective protection of 4, 6 dihydroxy of acetylgalactosamine residue of the compound of Formula D, in the presence of R₁C(O)H or R₁C(O)H dialiphatic alcohol, and under acid catalysis, to obtain a compound of Formula E;

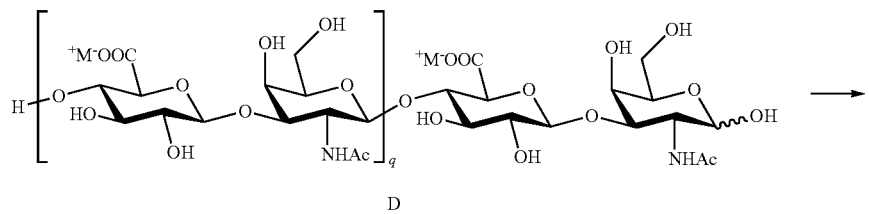

D

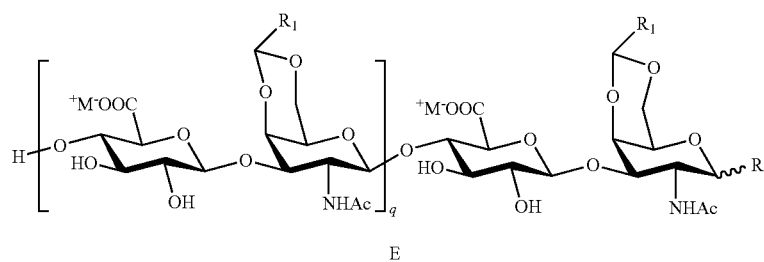

E (5) cyclizing the compound of Formula E with the presence of anhydride R₂—O—R₂, followed by lactone ring opening in R₃OH solution under base catalysis, to obtain a compound of Formula F;

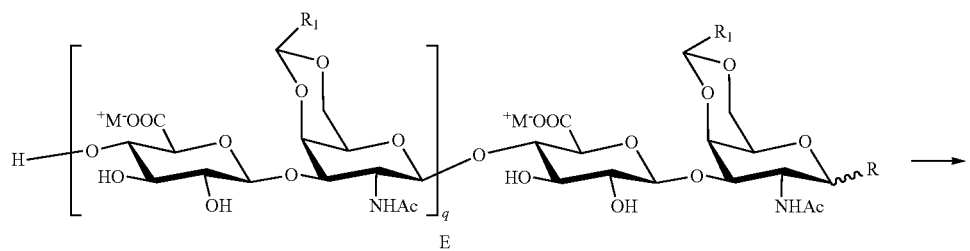

E

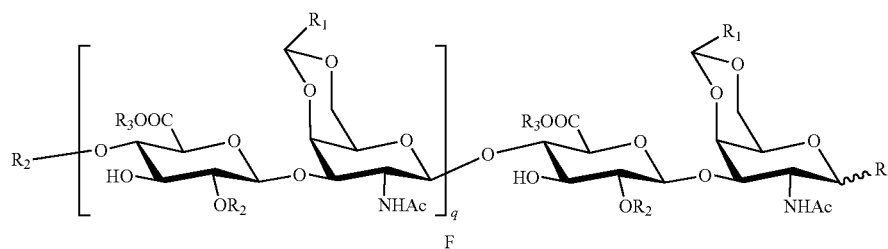

F (6) subjecting the compound of Formula F to react with a compound of Formula G as fucose donor, under acid catalysis, to obtain a compound of Formula H;

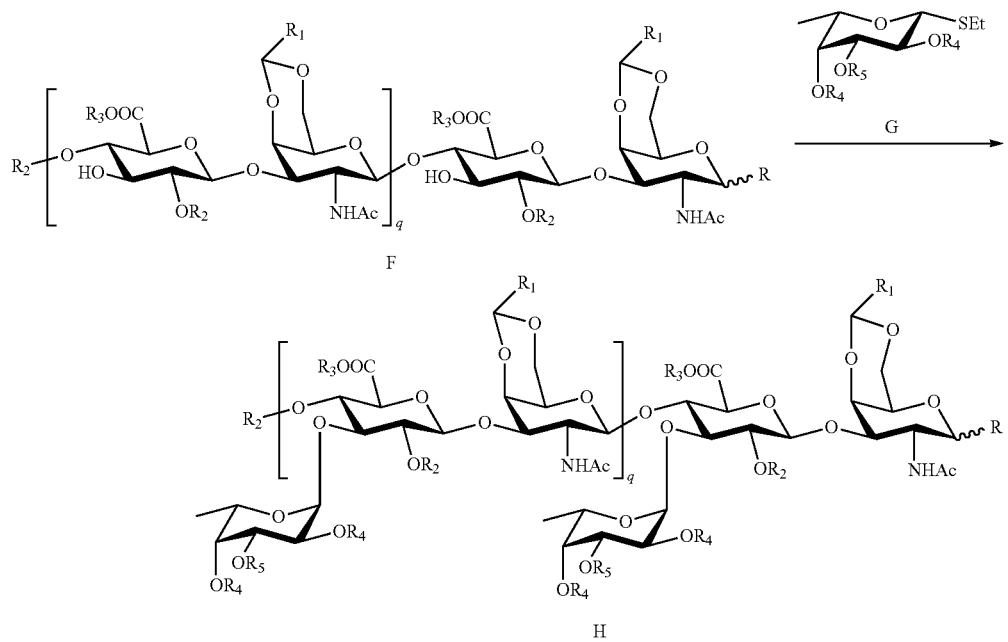
(7) removing galactosamine 4,6-OH protection from the compound of Formula H with the presence of an acid, followed by selectively removing the protective group $R_4$ on the fucose, to obtain a compound of Formula I;
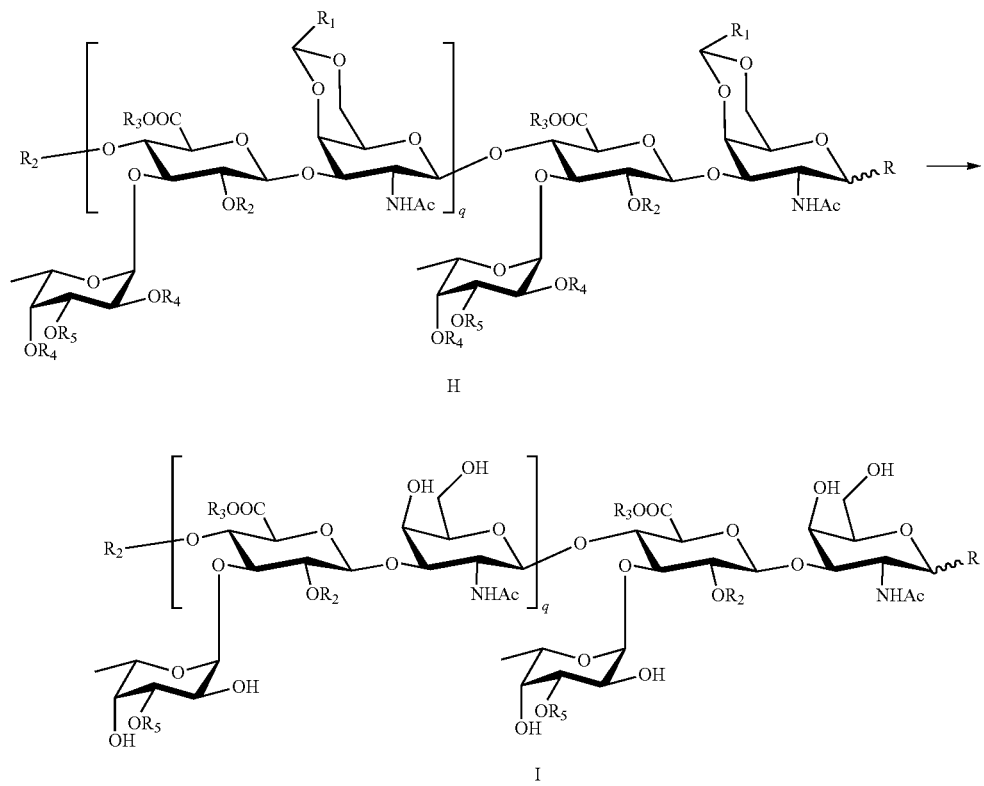
(8) subjecting the compound of Formula I to sulfation and deprotection, to obtain the compound of Formula J';

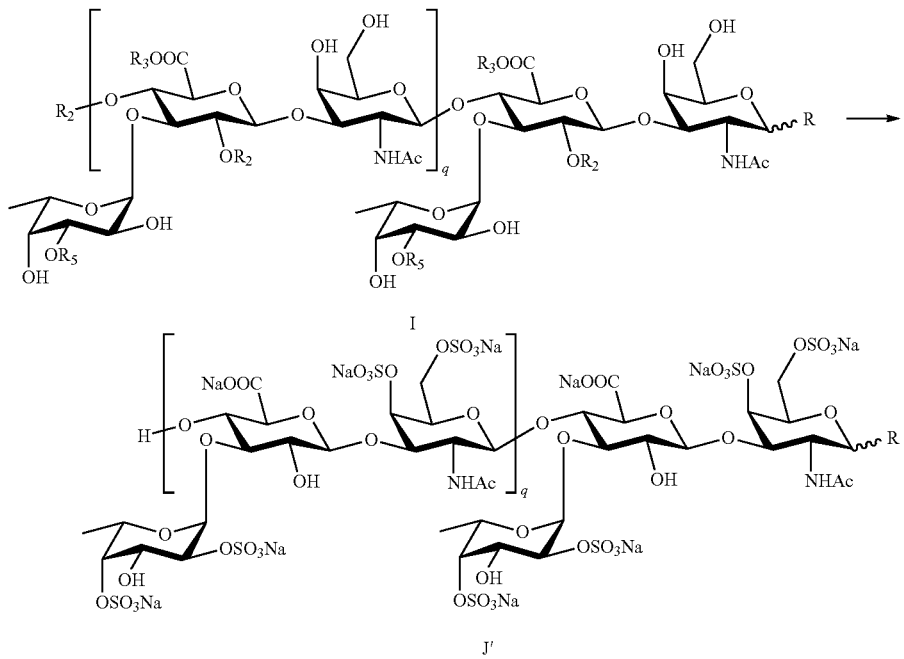

wherein, in the compounds of Formula D to Formula J and RX, R is azido, C1-C4 alkoxy, phenoxy, C1-C4 alkylthio, C1-C4 alkanoylthio, benzoyloxy or benzoylthio; wherein when R is azido, phenoxy, C1-C4 alkylthio, C1-C4 alkanoylthio, benzoyloxy, or benzoylthio, ⁓ is in β configuration; when R is C1-C4 alkoxy, ⁓ is in α configuration;

X in RX is hydrogen or alkali metal;

in $R_1C(O)H$ or $R_1C(O)H$ dialiphatic alcohol and the compounds of Formula E to Formula H, $R_1$ is unsubstituted phenyl or substituted phenyl, wherein the substituted phenyl refers to a benzene ring being substituted by one or two or more substituents selected from one or more of halogen, nitro, C1-C4 alkyl, C1-C4 haloalkyl and C1-C4 alkoxy; and, optionally, the substituent is at any position of the benzene ring;

in the anhydride $R_2$—O—$R_2$, or the compounds of Formula F to Formula I, $R_2$ is selected from one of aliphatic acyl, unsubstituted benzoyl or substituted benzoyl, and acetylpropionyl; wherein, the aliphatic acyl refers to C2-C6 alkanoyl; the substituted benzoyl refers to the benzene ring being substituted by one or two or more substituents selected from one or more of halogen, nitro, C1-C4 alkyl, C1-C4 haloalkyl and C1-C4 alkoxy; and, optionally, the substituent is at any position of the benzene ring;

in $R_3OH$, or the compounds of Formula F to Formula I, $R_3$ is selected from one of unsubstituted benzyl or substituted benzyl, C1-C4 alkyl, C1-C4 alkoxy and allyl; wherein the substituted benzyl refers to the benzene ring being substituted by one or two or more substituents selected from one or more of halogen, nitro, C1-C4 alkyl, C1-C4 haloalkyl, and C1-C4 alkoxy; and, optionally, the substituent is at any position of the benzene ring;

in the compounds of Formula G to Formula H, $R_4$ is selected from unsubstituted benzyl or substituted benzyl; the substituted benzyl refers to the benzene ring being substituted by one or two or more substituents selected from one or more of halogen, nitro, C1-C4 alkyl, C1-C4 haloalkyl and C1-C4 alkoxy; and, optionally, the substituent is at any position of the benzene ring;

in the compounds of Formula G to Formula I, $R_5$ is selected from one of aliphatic acyl, unsubstituted benzoyl or substituted benzoyl, and acetylpropionyl; wherein the aliphatic acyl refers to C2-C6 alkanoyl; the substituted benzoyl refers to the benzene ring being substituted by one or two or more substituents selected from one or more of halogen, nitro, C1-C4 alkyl, C1-C4 haloalkyl and C1-C4 alkoxy; and, optionally, the substituent is at any position of the benzene ring;

Et in the compound of Formula G is ethyl;

in Formula A to Formula D and MOH base, M is sodium, potassium, lithium or calcium.

9. The synthesis method of the fucosylated chondroitin sulfate oligosaccharide of claim 8, wherein in step (1), the inorganic acid is selected from one or more of hydrogen chloride, sulfuric acid, nitric acid and phosphoric acid; the C1-C4 alkanol is methanol or ethanol; and the MOH base is NaOH, KOH, or LiOH.

10. The synthesis method of the fucosylated chondroitin sulfate oligosaccharide of claim 8, wherein in step (2), the hyaluronidase has an activity of 400-1000 IU/mg, and is added in an amount of 2.0-3.0% of the mass of chondroitin, i.e., the compound of Formula B, and the reaction temperature is 37° C.; weakly acidic refers to the pH value of the buffer solution being 3.0-6.5; the buffer solution refers to one of: acetic acid-sodium acetate buffer, acetic acid-potassium acetate buffer, sodium dihydrogen phosphate-disodium hydrogen phosphate buffer or potassium dihydrogen phosphate-dipotassium hydrogen phosphate buffer; the concentration of the buffer is selected from 0.01 M to 1 M; sodium chloride of a concentration refers to a concentration of sodium chloride selected from 0.05 M to 0.5 M; the hyaluronidase is selected from a hyaluronidase originating from animal testis;

optionally, in step (3), when RX is sodium azide, sodium phenolate, sodium C1-C4 alkylthio, sodium C1-C4 alkanoylthio, sodium benzoate or sodium benzoylthio, the compound of Formula C reacts with sodium azide, sodium phenolate, sodium C1-C4 alkylthio, sodium C1-C4 alkanoylthio, sodium benzoate or sodium benzoylthio, in a basic solution with the presence of 2-chloro-1,3-dimethyl imidazoline chloride, to obtain the compound of Formula D, and in the compound of Formula D, ᴧᴧᴧ is in β configuration; wherein the organic base used in the basic solution is selected from one or more of triethylamine, N-methylmorpholine, pyridine, 2,6-dimethylpyridine and diisopropylethylamine; when RX is C1-C4 alkyl alcohol, the compound of Formula C reacts overnight in an alkyl alcohol solution of HCl, and then releases carboxyl under a basic condition, to obtain the compound of Formula D, and in the compound of Formula D, ᴧᴧᴧ is in α configuration; wherein the inorganic base used under the basic condition is selected from one or more of sodium hydroxide, potassium hydroxide and lithium hydroxide;

optionally, in step (4), under acid catalysis refers to being in the presence of the following protic acids or Lewis acids;

optionally, the base used in step (5) is selected from one or more of sodium methoxide and sodium acetate;

optionally, in the step (6), under acid catalysis refers to being in the presence of the following protic acids or Lewis acids: one or more selected from trifluoromethanesulfonic acid, alkylsilyl trifluoromethanesulfonate, metal salt of trifluoromethanesulfonate and boron trifluoride etherate; the reaction is carried out in an organic solvent selected from one or more of dichloromethane, N, N-dimethylformamide, chloroform, diethyl ether and toluene;

optionally, in step (7), the acid used is selected from one or more of acetic acid, camphorsulfonic acid and p-toluenesulfonic acid; the reagent used for "selectively removing the protective group $R_4$ on fucose" is selected from one of ceric ammonium nitrate and DDQ;

optionally, in step (8), the reagent used for sulfation is selected from one of pyridine sulfur trioxide complex, sulfur trioxide trimethylamine complex and sulfur trioxide triethylamine complex, and the sulfation is optionally carried out in anhydrous pyridine or anhydrous DMF; deprotection is carry out in a mixed solvent of tetrahydrofuran and water, wherein ratio of tetrahydrofuran to water is 3:1-2:1, and the base is one or two of lithium hydroxide and sodium hydroxide.

11. An intermediate compound for synthesizing fucosylated chondroitin sulfate oligosaccharide, wherein the intermediate compound is selected from one of the compounds of Formula D to Formula I:

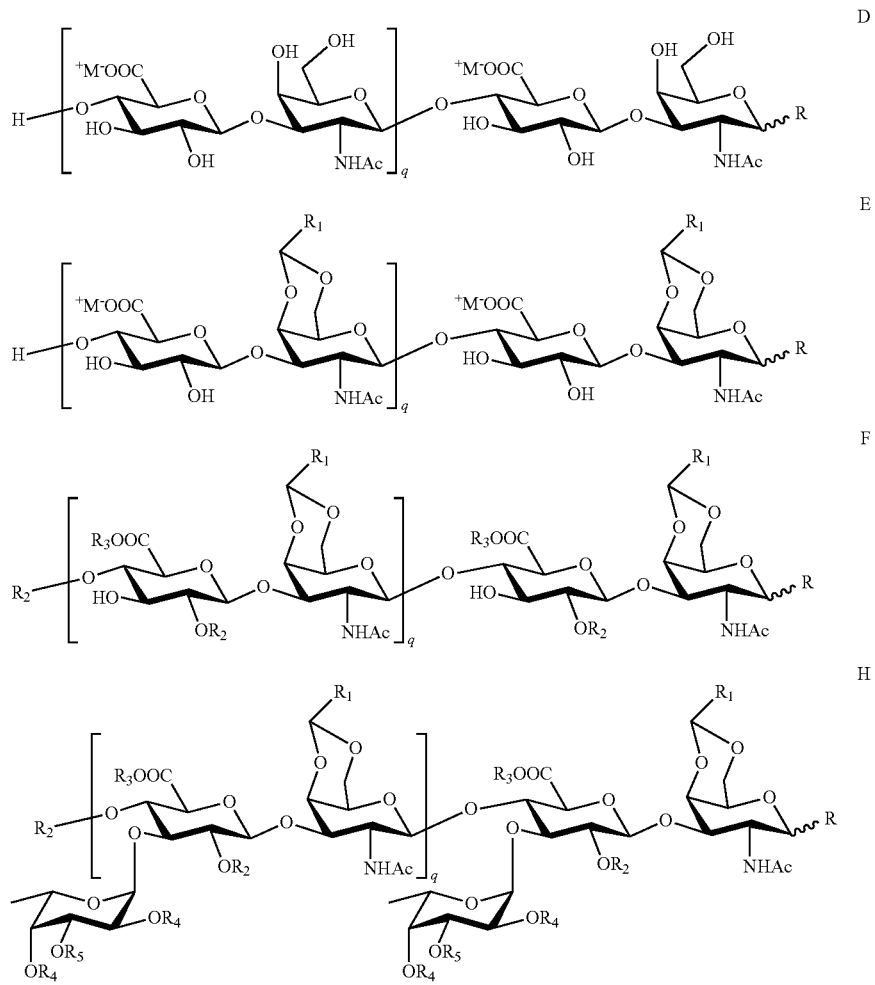

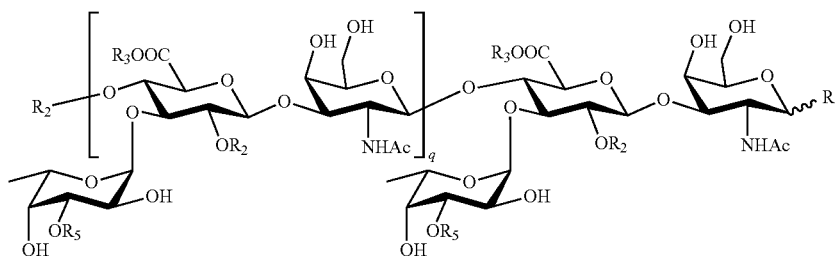

wherein, the definition of each substituent in the compounds of Formula D to Formula I is as defined in claim 8.

12. The intermediate compound of claim 11, wherein the intermediate compound is selected from one of the following compounds:

azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)] disodium salt;

azido[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-β-D-galactopyranosyl) trisodium salt;

azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)] disodium salt;

azido[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-β-D-galactopyranosyl)] trisodium salt;

azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)];

azido[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-β-D-galactopyranosyl)];

azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]};

azido{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-β-D-galactopyranosyl)]};

azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]};

azido{(3-O-acetylpropionyl-α-L-fucosyl)-(1→3)-(2,4-di-O-benzoyl-β-D-methyl glucopyranosyluronate)-(1→3)-(2-deoxy-2-N-acetamino-β-D-galactopyranosyl)-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]-(1→4)-[(3-O-acetylpropionyl-α-L-fucosyl)-(1→3)-(2-O-benzoyl-β-D-methyl glucopyranosyluronate)-(1→3)-(2-deoxy-2-N-acetamido-β-D-galactopyranosyl)]};

methyl-[(β-D-glucopyranosyluronic acid)-(1→3)-(2-deoxy-2-N-acetamido-β-D-galactopyranosyl)-(1→4)-(β-D-glucopyranosyluronic acid)-(1→3)-(2-deoxy-2-N-acetamido-α-D-galactopyranosyl)] disodium salt;

methyl-[(β-D-glucopyranosyluronic acid)-(1→3)-(4,6-O-benzylidene-2-deoxy-2-N-acetamido-β-D-galactopyranosyl)-(1→4)-(β-D-glucopyranosyluronic acid)-(1→3)-(4,6-O-benzylidene-2-deoxy-2-N-acetamido-α-D-galactopyranosyl)] disodium salt;

methyl-[(2,4-di-O-benzoyl-β-D-methyl glucopyranosyluronate)-(1→3)-(4,6-O-benzylidene-2-deoxy-2-N-acetamido-β-D-galactopyranosyl)-(1→4)-(2-O-benzoyl-β-D-methyl glucopyranosyluronate)-(1→3)-(4,6-O-benzylidene-2-deoxy-2-N-acetamido-α-D-galactopyranosyl)];

methyl-{(2,4-di-O-p-methoxybenzyl-3-O-acetylpropionyl-α-L-fucosyl)-(1→3)-(2,4-di-O-benzoyl-β-D-methyl glucopyranosyluronate)-(1→3)-(4,6-O-benzylidene-2-deoxy-2-N-acetamino-β-D-galactopyranosyl)-(1→4)-[(2,4-di-O-p-methoxybenzyl-3-O-acetylpropionyl-α-L-fucosyl)-(1→3)-(2-O-benzoyl-β-D-methyl glucopyranosyluronate)-(1→3)-(4,6-O-benzylidene-2-deoxy-2-N-acetamido-α-D-galactopyranosyl)]}; and methyl-{(3-O-acetylpropionyl-α-L-fucosyl)-(1→3)-(2,4-di-O-benzoyl-β-D-methyl glucopyranosyluronate)-

(1→3)-(2-deoxy-2-N-acetamino-β-D-galactopyrano-
syl)-(1→4)-[(3-O-acetylpropionyl-α-L-fucosyl)-
(1→3)-(2-O-benzoyl-β-D-methyl
glucopyranosyluronate)-(1→3)-(2-deoxy-2-N-acet-
amido-α-D-galactopyranosyl)]}.

13. A pharmaceutical composition comprising the fucosylated chondroitin sulfate oligosaccharide of claim 1.

14. A method of anticoagulation, comprising administering the pharmaceutical composition of claim 13 to a subject in need thereof.

15. A method of anticoagulation, comprising administering the fucosylated chondroitin sulfate oligosaccharide of claim 1 to a subject in need thereof.

\* \* \* \* \*